US012683191B2

(12) United States Patent
Shimizu et al.

(10) Patent No.: US 12,683,191 B2
(45) Date of Patent: Jul. 14, 2026

(54) NONAQUEOUS ELECTROLYTE SOLUTION FOR LITHIUM SECONDARY BATTERIES, LITHIUM SECONDARY BATTERY PRECURSOR, LITHIUM SECONDARY BATTERY, AND METHOD FOR MANUFACTURING LITHIUM SECONDARY BATTERY

(71) Applicants: MITSUI CHEMICALS, INC., Tokyo (JP); DAIKIN INDUSTRIES, LTD., Osaka (JP)

(72) Inventors: Yusuke Shimizu, Ichihara (JP); Hidenobu Nogi, Chiba (JP); Masahiro Suguro, Tokyo (JP); Yoshiko Kuwajima, Osaka (JP); Tomoya Hidaka, Osaka (JP); Kae Fujiwara, Osaka (JP); Shigeaki Yamazaki, Osaka (JP)

(73) Assignees: MITSUI CHEMICALS, INC., Tokyo (JP); DAIKIN INDUSTRIES, LTD., Osaka (JP)

( * ) Notice: Subject to any disclaimer, the term of this patent is extended or adjusted under 35 U.S.C. 154(b) by 442 days.

(21) Appl. No.: 18/263,926

(22) PCT Filed: Jan. 17, 2022

(86) PCT No.: PCT/JP2022/001416
§ 371 (c)(1),
(2) Date: Aug. 2, 2023

(87) PCT Pub. No.: WO2022/168584
PCT Pub. Date: Aug. 11, 2022

(65) Prior Publication Data
US 2024/0154164 A1 May 9, 2024

(30) Foreign Application Priority Data
Feb. 2, 2021 (JP) ................................ 2021-015328

(51) Int. Cl.
*H01M 10/0567* (2010.01)
*C07D 323/02* (2006.01)
(Continued)

(52) U.S. Cl.
CPC ...... *H01M 10/0567* (2013.01); *C07D 323/02* (2013.01); *C07D 327/10* (2013.01);
(Continued)

(58) Field of Classification Search
CPC ............. H01M 10/0567; C07D 323/02; C07D 327/10; C07F 1/02; C07F 5/022
See application file for complete search history.

(56) References Cited

U.S. PATENT DOCUMENTS

| | | | | |
|---|---|---|---|---|
| 9,227,950 | B2 * | 1/2016 | Mio | H01M 10/0525 |
| 11,916,195 | B2 * | 2/2024 | Kinoshita | H01M 10/0567 |

(Continued)

FOREIGN PATENT DOCUMENTS

| | | | |
|---|---|---|---|
| EP | 3514880 | A1 | 7/2019 |
| EP | 3557683 | A1 | 10/2019 |

(Continued)

OTHER PUBLICATIONS

Zhao, H. et al. "Film-forming electrolyte additives for rechargeable lithium-ion batteries: progress and outlook" Journal of Materials Chemistry A, vol. 7, Mar. 13, 2019, pp. 8700-8722.

*Primary Examiner* — Amanda C. Walke
(74) *Attorney, Agent, or Firm* — BUCHANAN INGERSOLL & ROONEY PC

(57) ABSTRACT

Provided is a nonaqueous electrolyte solution for a lithium secondary battery, the nonaqueous electrolyte solution containing a compound (I) represented by Formula (I) and a compound (II) represented by Formula (II). In Formula (I), each of $R^1$ and $R^2$ independently represents a substituent
(Continued)

such as an alkyl group having from 1 to 7 carbon atoms. In Formula (II), $R^3$ represents an oxygen atom or the like; $R^4$ represents a group represented by Formula (ii-1), a group represented by Formula (ii-2), or the like; and * represents a binding position. In Formula (ii-1), $R^{41}$ represents an oxymethylene group or the like and, in Formula (ii-2), $R^{42}$ represents an alkyl group having from 1 to 6 carbon atoms, or the like.

(I)

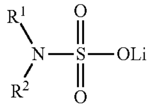

(II)

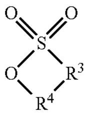

(ii-1)

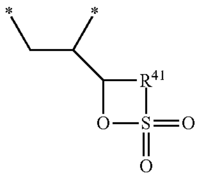

(ii-2)

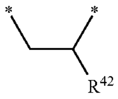

11 Claims, 1 Drawing Sheet

(51) Int. Cl.

| | |
|---|---|
| ***C07D 327/10*** | (2006.01) |
| ***C07F 1/02*** | (2006.01) |
| ***C07F 5/02*** | (2006.01) |
| ***H01M 10/0525*** | (2010.01) |
| ***H01M 10/058*** | (2010.01) |
| ***H01M 10/44*** | (2006.01) |

(52) U.S. Cl.

CPC ................ *C07F 1/02* (2013.01); *C07F 5/022* (2013.01); *H01M 10/0525* (2013.01); *H01M 10/058* (2013.01); *H01M 10/44* (2013.01); *H01M 2300/0025* (2013.01)

(56) References Cited

U.S. PATENT DOCUMENTS

| | | | | |
|---|---|---|---|---|
| 2012/0064396 | A1* | 3/2012 | Nishie | H01M 10/0568 429/199 |
| 2013/0171514 | A1 | 7/2013 | Mio et al. | |
| 2017/0200974 | A1 | 7/2017 | Maruo et al. | |
| 2018/0138551 | A1* | 5/2018 | Miyasato | H01M 10/0569 |
| 2021/0043971 | A1 | 2/2021 | Fujiyama et al. | |
| 2021/0043974 | A1* | 2/2021 | Kinoshita | H01G 11/64 |
| 2021/0087059 | A1* | 3/2021 | Suzuki | C01B 17/98 |
| 2021/0296703 | A1 | 9/2021 | Sugawara et al. | |
| 2021/0391597 | A1* | 12/2021 | Hidaka | H01G 11/60 |
| 2021/0399344 | A1 | 12/2021 | Hidaka et al. | |

FOREIGN PATENT DOCUMENTS

| | | | |
|---|---|---|---|
| EP | 3605707 | A1 | 2/2020 |
| EP | 3761435 | A1 | 1/2021 |
| EP | 3764451 | A1 | 1/2021 |
| JP | 3439085 | B2 | 8/2003 |
| JP | 2018078108 | A | 5/2018 |
| JP | 2018081920 | A | 5/2018 |
| KR | 20200121358 | A | 10/2020 |
| WO | 2012053644 | A1 | 4/2012 |
| WO | 2018181369 | A1 | 10/2018 |
| WO | 2020022452 | A1 | 1/2020 |
| WO | 2020/175522 | A1 | 9/2020 |

* cited by examiner

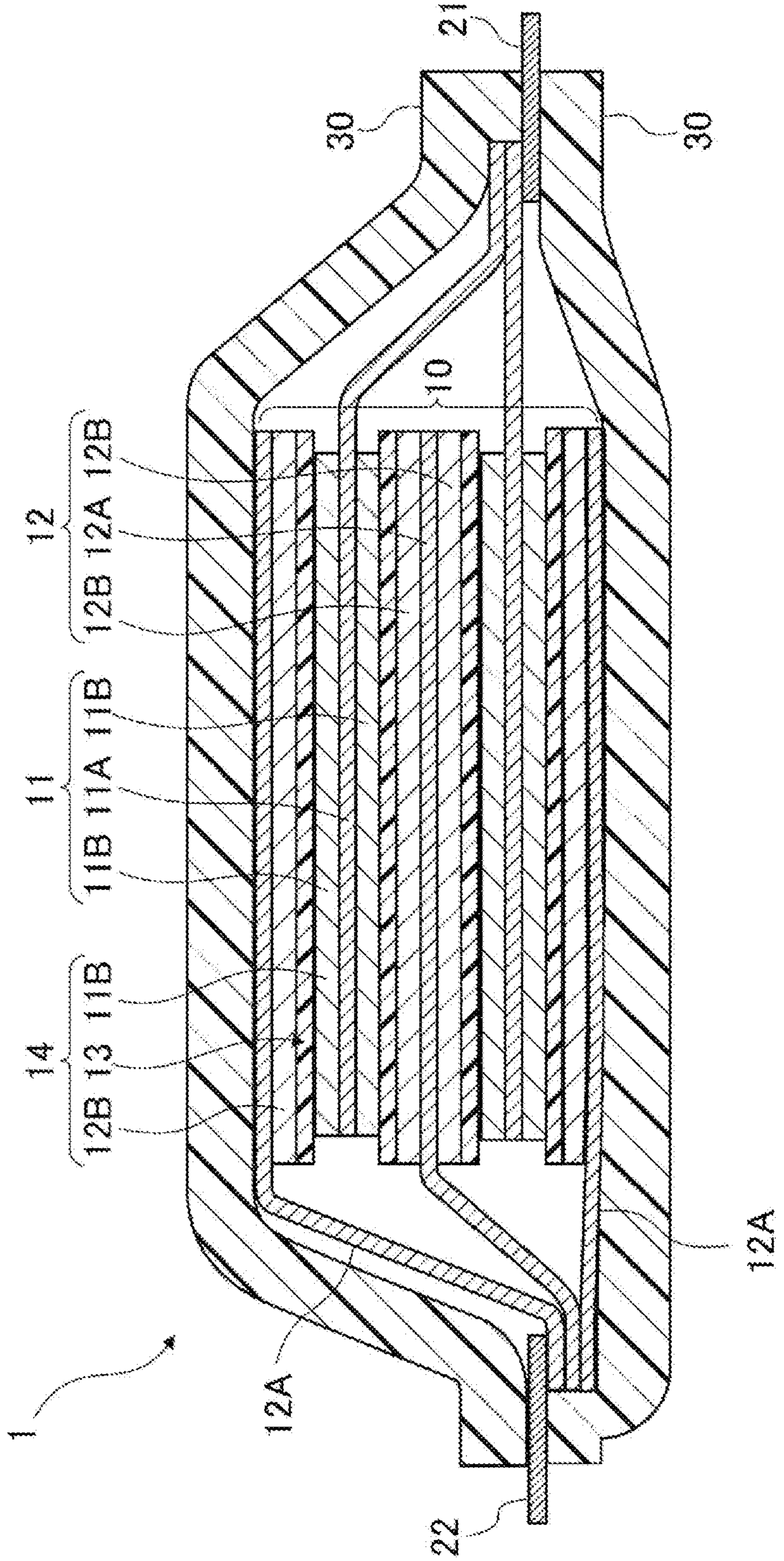
21
30
30
10
12
12B
12A
12B
11
11B
11A
11B
14
11B
13
12B
12A
12A
1
22

NONAQUEOUS ELECTROLYTE SOLUTION FOR LITHIUM SECONDARY BATTERIES, LITHIUM SECONDARY BATTERY PRECURSOR, LITHIUM SECONDARY BATTERY, AND METHOD FOR MANUFACTURING LITHIUM SECONDARY BATTERY

TECHNICAL FIELD

The present disclosure relates to: a nonaqueous electrolyte solution for a lithium secondary battery; a lithium secondary battery precursor; a lithium secondary battery; and a method of producing a lithium secondary battery.

BACKGROUND ART

Lithium secondary batteries have been attracting attention as batteries having a high energy density.

Patent Document 1 discloses a nonaqueous electrolyte secondary battery. The nonaqueous electrolyte secondary battery disclosed in Patent Document 1 includes a positive electrode, a negative electrode, and a nonaqueous electrolyte solution. The negative electrode is formed of lithium or a negative electrode material capable of occluding and releasing lithium. The nonaqueous electrolyte solution is composed of an organic solvent and a solute. The organic solvent contains at least one additive selected from the group consisting of lithium monofluorophosphate and lithium difluorophosphate.

Patent Documents 2 and 3 disclose electrolyte solutions used in lithium secondary batteries. The electrolyte solutions disclosed in Patent Documents 2 and 3 contain a solvent, an electrolyte salt, and a compound represented by $(C_2H_5)_2NSO_3Li$ in an amount of from 0.001 to 10% by mass with respect to the amount of the solvent.

Patent Document 4 discloses a nonaqueous electrolyte solution. The nonaqueous electrolyte solution disclosed in Patent Document 4 contains a specific cyclic sulfate compound.

Patent Document 5 discloses a nonaqueous electrolyte solution for batteries. The nonaqueous electrolyte solution for batteries disclosed in Patent Document 5 contains an additive A, an additive B, and an additive C. The additive A is at least one selected from the group consisting of specific fluorinated cyclic carbonates. The additive B is at least one selected from the group consisting of lithium monofluorophosphate and lithium difluorophosphate. The additive C is at least one selected from the group consisting of compounds having a sulfur-oxygen bond.

Patent Document 1: Japanese Patent No. 3439085

Patent Document 2: Japanese Patent Application Laid-Open (JP-A) No. 2018-078108

Patent Document 3: JP-A No. 2018-081920

Patent Document 4: WO 2012/053644

Patent Document 5: WO 2020/022452

SUMMARY OF THE INVENTION

Technical Problem

In the nonaqueous electrolyte secondary battery disclosed in Patent Document 1, storage thereof in a high-temperature environment may cause an increase in the internal resistance and a decrease in the capacity.

The electrolyte solutions disclosed in Patent Documents 2 to 4 provide excellent battery performance in a high-temperature environment. However, in response to diversification and the like of the use of lithium secondary batteries in recent years, there is a demand for a nonaqueous electrolyte solution of a lithium secondary battery, which does not cause deterioration of the battery performance even when the lithium secondary battery is stored in a high-temperature environment over an extended period (e.g., 14 days or longer).

In view of the above-described circumstances, an object of the disclosure is to provide: a nonaqueous electrolyte solution for a lithium secondary battery, with which a decrease in the capacity and an increase in the internal resistance of a lithium secondary battery can be inhibited even when the lithium secondary battery is stored in a high-temperature environment over an extended period (e.g., 14 days or longer); a lithium secondary battery precursor; a lithium secondary battery; and a method of producing a lithium secondary battery.

Solution to Problem

Means for solving the above-described problem include the following embodiments.

<1> A nonaqueous electrolyte solution for a lithium secondary battery, the solution containing:

a compound (I) represented by the following Formula (I); and a compound (II) represented by the following Formula (II):

(I)

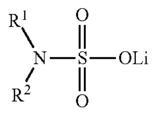

wherein, in Formula (I):

each of $R^1$ and $R^2$ independently represents a substituent that is

—H,

—F, a group represented by the Formula: $—O_p—(SiR^{11}_2O)_t—SiR^{12}_3$, wherein each of $R^{11}$ and $R^{12}$ independently represents an alkyl group in which at least one hydrogen atom is optionally substituted with a fluorine atom, an alkenyl group in which at least one hydrogen atom is optionally substituted with a fluorine atom, an alkynyl group in which at least one hydrogen atom is optionally substituted with a fluorine atom, or an aryl group in which at least one hydrogen atom is optionally substituted with a fluorine atom; t represents an integer that is 0 or larger; and p represents 0 or 1, an alkyl group having from 1 to 7 carbon atoms, an alkenyl group having from 2 to 7 carbon atoms, an alkynyl group having from 2 to 7 carbon atoms, an aryl group having from 6 to 15 carbon atoms, a group represented by $—SO_2X^1$, wherein $X^1$ represents —H, —F, or an alkyl group in which at least one hydrogen atom is optionally substituted with a fluorine atom, a group represented by $—SO_3X^2$, wherein $X^2$ represents —H, —F, or an alkyl group in which at least one hydrogen atom is optionally substituted with a fluorine atom, or a hydrocarbon group having from 2 to 7 carbon atoms in which $R^1$ and $R^2$ are bound to each other to form a cyclic structure that optionally contains a multiple bond, and the substituent has a structure which optionally contains at least one di- to hexa-valent heteroatom, and in which at least one hydrogen atom is optionally substituted with a fluorine atom or a functional group having from 0 to 7 carbon atoms;

(II)

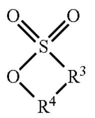

wherein, in Formula (II):

$R^3$ represents an oxygen atom, an alkylene group having from 2 to 6 carbon atoms, or an alkenylene group having from 2 to 6 carbon atoms, $R^4$ represents an alkylene group having from 2 to 6 carbon atoms, an alkenylene group having from 2 to 6 carbon atoms, a group represented by the following Formula (ii-1), or a group represented by the following Formula (ii-2), and

* represents a binding position, (ii-1)

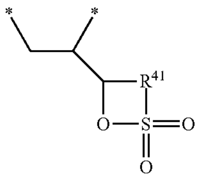

(ii-2)

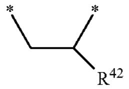

wherein, in Formula (ii-1), $R^{41}$ represents an oxygen atom, an alkylene group having from 1 to 6 carbon atoms, an alkenylene group having from 2 to 6 carbon atoms, or an oxymethylene group, and wherein, in Formula (ii-2), $R^{42}$ represents an alkyl group having from 1 to 6 carbon atoms, or an alkenyl group having from 2 to 6 carbon atoms.

<2> The nonaqueous electrolyte solution for a lithium secondary battery according to <1>, wherein $R^3$ is an oxygen atom.

<3> The nonaqueous electrolyte solution for a lithium secondary battery according to <1> or <2>, wherein a content of the compound (I) is from 0.01% by mass to 5% by mass with respect to a total amount of the nonaqueous electrolyte solution for a lithium secondary battery.

<4> The nonaqueous electrolyte solution for a lithium secondary battery according to any one of <1> to <3>, wherein a content of the compound (II) is from 0.01% by mass to 5% by mass with respect to a total amount of the nonaqueous electrolyte solution for a lithium secondary battery.

<5> The nonaqueous electrolyte solution for a lithium secondary battery according to any one of <1> to <4>, containing a compound (III) represented by the following Formula (III):

(III)

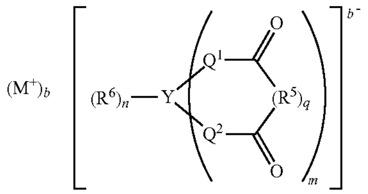

wherein, in Formula (III):

M represents an alkali metal,

Y represents a transition element, or an element of Group 13, 14, or 15 of the periodic table, b represents an integer from 1 to 3, m represents an integer from 1 to 4, n represents an integer from 0 to 8, q represents 0 or 1, $R^5$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, the halogenated alkylene group, the arylene group and the halogenated arylene group each optionally containing a substituent or a heteroatom in structure thereof and, when q is 1 and m is from 2 to 4, m instances $R^5$ are optionally bound to each other, $R^6$ represents a halogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, the halogenated alkyl group, the aryl group and the halogenated aryl group each optionally containing a substituent or a heteroatom in a structure thereof and, when n is from 2 to 8, n instances of $R^6$ are optionally bound to each other to form a ring, and each of $Q^1$ and $Q^2$ independently represents an oxygen atom or a carbon atom.

<6> The nonaqueous electrolyte solution for a lithium secondary battery according to <5>, wherein a content of the compound (III) is from 0.01% by mass to 10% by mass with respect to a total amount of the nonaqueous electrolyte solution for a lithium secondary battery.

<7> The nonaqueous electrolyte solution for a lithium secondary battery according to any one of <1> to <6>, containing a compound (IV) represented by the following Formula (IV):

(IV)

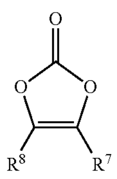

wherein, in Formula (IV), each of $R^7$ and $R^8$ independently represents a hydrogen atom, a methyl group, an ethyl group, or a propyl group.

<8> The nonaqueous electrolyte solution for a lithium secondary battery according to <7>, wherein a content of the compound (IV) is from 0.01% by mass to 10% by mass with respect to a total amount of the nonaqueous electrolyte solution for a lithium secondary battery.

<9> A lithium secondary battery precursor, including:

a positive electrode;

a negative electrode containing a negative electrode active material capable of occluding and releasing lithium ions; and the nonaqueous electrolyte solution for a lithium secondary battery according to any one of <1> to <8>.

<10> A lithium secondary battery, obtained by charging and discharging the lithium secondary battery precursor according to <9>.

<11> A method of producing a lithium secondary battery, the method including: a step of preparing the lithium secondary battery precursor according to <9>; and a step of charging and discharging the lithium secondary battery precursor.

Advantageous Effects of Invention

According to the disclosure, the following are provided: a nonaqueous electrolyte solution for a lithium secondary battery, with which a decrease in the capacity and an increase in the internal resistance of a lithium secondary battery can be inhibited even when the lithium secondary battery is stored in a high-temperature environment over an extended period; a lithium secondary battery precursor; a lithium secondary battery; and a method of producing a lithium secondary battery.

BRIEF DESCRIPTION OF DRAWING

FIG. 1 is a cross-sectional view of the lithium secondary battery precursor according to one embodiment of the disclosure.

DESCRIPTION OF EMBODIMENTS

Hereinafter, embodiments of the nonaqueous electrolyte solution for a lithium secondary battery, the lithium secondary battery precursor, the lithium secondary battery, and the method of producing a lithium secondary battery, which are according to the disclosure, are described referring to the drawing. In the drawing, the same or corresponding parts are denoted by the same reference symbol, and description thereof is not repeated.

In the present specification, those numerical ranges that are expressed with "to" each denote a range that includes the numerical values stated before and after "to" as the lower limit value and the upper limit value, respectively.

[Nonaqueous Electrolyte Solution for Lithium Secondary Battery]

The nonaqueous electrolyte solution for a lithium secondary battery according to the present embodiment (hereinafter, referred to as "nonaqueous electrolyte solution") will now be described.

The nonaqueous electrolyte solution is used as an electrolyte solution of a lithium secondary battery. The details of the lithium secondary battery will be described below referring to FIG. 1.

The nonaqueous electrolyte solution contains a compound (I) represented by Formula (I) (hereinafter, referred to as "nitrogen-containing lithium salt compound (I)") and a compound (II) represented by Formula (II) (hereinafter, referred to as "cyclic sulfur-containing ester compound (II)"). The details of each of the nitrogen-containing lithium salt compound (I) and the cyclic sulfur-containing ester compound (II) will be described below.

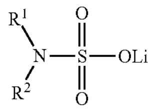

(I)

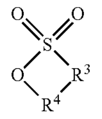

(II)

The nonaqueous electrolyte solution contains the nitrogen-containing lithium salt compound (I) and the cyclic sulfur-containing ester compound (II) and, therefore, can inhibit a decrease in the capacity and an increase in the internal resistance of a lithium secondary battery even when the lithium secondary battery is stored in a high-temperature environment over an extended period.

It is presumed that this effect is exerted because of the following.

When a lithium secondary battery is produced using the nonaqueous electrolyte solution according to the present embodiment, it is believed that, in the production process (e.g., the below-described aging step), a reaction product is generated in the vicinity of the surface of a negative electrode of the lithium secondary battery, and a component that is a decomposition product of the reaction product is generated as well. This reaction product refers to a product generated by a reaction of the nitrogen-containing lithium salt compound (I), the cyclic sulfur-containing ester compound (II), and LiF generated from an electrolyte. Such a reaction product and the like adhere to the surface of the negative electrode to form a solid electrolyte interphase (SEI: Solid Electrolyte Interphase) film (hereinafter, referred to as "SEI film"). It is believed that, in the production process, this component migrates to the vicinity of the surface of a positive electrode, adheres to the surface of the positive electrode, and forms a cathode solid electrolyte interphase (CEI: Cathode Electrolyte Interphase) (hereinafter, referred to as "CEI film").

By this, a side reaction, which is not a natural battery reaction, is made unlikely to proceed even in a charge-discharge cycle performed after storage of the lithium secondary battery in a high-temperature environment. The "battery reaction" refers to a reaction causing lithium ions to move in and out of the positive electrode and the negative electrode (intercalation). Examples of the side reaction include: a reductive decomposition reaction of the electrolyte solution by the negative electrode; an oxidative decomposition reaction of the electrolyte solution by the positive electrode; and elution of a metal element contained in a positive electrode active material.

Even in a charge-discharge cycle performed after storage of the lithium secondary battery in a high-temperature environment, the SEI film and the CEI film are both unlikely to be increased in thickness. Therefore, lithium ions contained in the electrolyte solution are unlikely to be consumed.

Because of the above-described reason, according to the nonaqueous electrolyte solution according to the present embodiment, a decrease in the capacity and an increase in the internal resistance of a lithium secondary battery are inhibited even when the lithium secondary battery is stored in a high-temperature environment over an extended period.

Hereinafter, when an “SEI film” and a “CEI film” are not distinguished from each other, the “SEI film” and the “CEI film” are collectively referred to as “SEI film and the like”.

The nonaqueous electrolyte solution preferably contains a compound (III) represented by Formula (III) (hereinafter, referred to as “cyclic dicarbonyl compound (III)”). The details of this compound (III) will be described below.

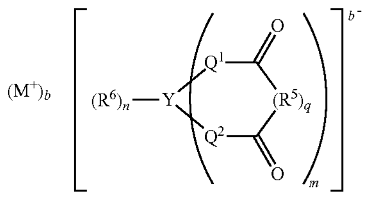

(III)

The nonaqueous electrolyte solution contains the cyclic dicarbonyl compound (III) in addition to the nitrogen-containing lithium salt compound (I) and the cyclic sulfur-containing ester compound (II), and thereby further inhibits a decrease in the capacity and an increase in the internal resistance of a lithium secondary battery even in a charge-discharge cycle performed after storage of the lithium secondary battery in a high-temperature environment.

It is presumed that this effect is exerted because of the following.

When the nonaqueous electrolyte solution contains the cyclic dicarbonyl compound (III) in addition to the nitrogen-containing lithium salt compound (I) and the cyclic sulfur-containing ester compound (II), the SEI film and the like can contain therein bonds derived from the cyclic dicarbonyl compound (III) in addition to the above-described reaction product and the like. This makes a thermally and chemically stable inorganic salt or polymer structure more likely to be formed. Therefore, in a high-temperature environment, for example, elution of a component of the SEI film and the like and modification of the SEI film and the like, which impair the durability of the SEI film and the like, are unlikely to occur. As a result, a decrease in the capacity and an increase in the internal resistance of the lithium secondary battery are further inhibited even in a charge-discharge cycle performed after storage of the lithium secondary battery in a high-temperature environment.

The nonaqueous electrolyte solution preferably contains a compound (IV) represented by Formula (IV) (hereinafter, referred to as “cyclic carbonate compound (IV)”). The details of this compound (IV) will be described below.

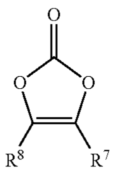

(IV)

The nonaqueous electrolyte solution contains the cyclic carbonate compound (IV) in addition to the nitrogen-containing lithium salt compound (I) and the cyclic sulfur-containing ester compound (II), and thereby further inhibits an increase in the internal resistance of a lithium secondary battery even in a charge-discharge cycle performed after long-term storage of the lithium secondary battery in a high-temperature environment.

It is presumed that this effect is exerted because of the following.

Even in a charge-discharge cycle performed after storage of the lithium secondary battery in a high-temperature environment, the cyclic carbonate compound (IV) is likely to be reductively decomposed by the negative electrode and form an SEI film and the like before the electrolyte solution is reductively decomposed on the negative electrode. By this, decomposition of the electrolyte solution on the negative electrode is inhibited. As a result, an increase in the internal resistance of the lithium secondary battery is further inhibited.

From the standpoint of further improving the dissociation of an electrolyte and the ion mobility, the nonaqueous electrolyte solution preferably has an intrinsic viscosity of 10.0 mPa’s or less at 25° C.

When a nonaqueous electrolyte solution recovered by disassembling a lithium secondary battery is actually analyzed, the amount of the nitrogen-containing lithium salt compound (I) and the cyclic sulfur-containing ester compound (II) therein may be less than the amount of these compounds added to the nonaqueous electrolyte solution. Even in such a case, as long as the nitrogen-containing lithium salt compound (I) and the cyclic sulfur-containing ester compound (II) are detected even in a small amount in the nonaqueous electrolyte solution extracted from the lithium secondary battery, the electrolyte solution of this lithium secondary battery is included in the scope of the nonaqueous electrolyte solution of the disclosure.

When a nonaqueous electrolyte solution recovered by disassembling a lithium secondary battery is actually analyzed, there is a case where at least either the nitrogen-containing lithium salt compound (I) or the cyclic sulfur-containing ester compound (II) cannot be detected from the nonaqueous electrolyte solution. Even in this case, as long as a compound derived from a decomposition product the nitrogen-containing lithium salt compound (I) and a compound derived from a decomposition product of the cyclic sulfur-containing ester compound (II) are detected in the nonaqueous electrolyte solution or in an SEI film and the like, the electrolyte solution of the lithium secondary battery is deemed to be included in the scope of the nonaqueous electrolyte solution of the disclosure. These measures are also the same for compounds other than the nitrogen-containing lithium salt compound (I) and the cyclic sulfur-containing ester compound (II) that may be contained in the nonaqueous electrolyte solution.

<Nitrogen-Containing Lithium Salt Compound (I)>

The nitrogen-containing lithium salt compound (I) is represented by Formula (I).

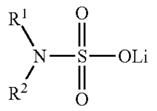

(I)

In Formula (I), each of $R^1$ and $R^2$ independently represents a substituent that is

—H,

—F, a group represented by the Formula: $—O_p—(SiR^{11}_2O)_t—SiR^{12}_3$, wherein each of $R^{11}$ and $R^{12}$ independently represents an alkyl group in which at least one hydrogen atom is optionally substituted with a fluorine atom, an alkenyl group in which at least one hydrogen atom is optionally substituted with a fluorine atom, an alkynyl group in which at least one hydrogen atom is optionally substituted with a fluorine atom, or an aryl group in which at least one hydrogen atom is optionally substituted with a fluorine atom; t represents an integer that is 0 or larger; and p represents 0 or 1, an alkyl group having from 1 to 7 carbon atoms, an alkenyl group having from 2 to 7 carbon atoms, an alkynyl group having from 2 to 7 carbon atoms, an aryl group having from 6 to 15 carbon atoms, a group represented by $—SO_2X^1$, wherein $X^1$ represents —H, —F, or an alkyl group in which at least one hydrogen atom is optionally substituted with a fluorine atom, a group represented by $—SO_3X^2$, wherein $X^2$ represents —H, —F, or an alkyl group in which at least one hydrogen atom is optionally substituted with a fluorine atom, or a hydrocarbon group having from 2 to 7 carbon atoms in which $R^1$ and $R^2$ are bound to each other to form a cyclic structure that optionally contains a multiple bond, and the substituent has a structure which optionally contains at least one di- to hexa-valent heteroatom, and in which at least one hydrogen atom is optionally substituted with a fluorine atom or a functional group having from 0 to 7 carbon atoms.

In other words, each of $R^1$ and $R^2$ is independently a prescribed substituent which optionally contains at least one di- to hexa-valent heteroatom in its structure, and in which at least one hydrogen atom is optionally substituted with a fluorine atom or a functional group having from 0 to 7 carbon atoms.

Specifically, $R^1$ and $R^2$ are each, for example, but not limited to: a linear alkyl group, a cyclic alkyl group, an alkenyl group, an alkynyl group, a halogenated alkyl group, a halogenated alkenyl group, a functional group-containing alkyl group, a saturated heterocyclic group-containing alkyl group, an aryl group, an aralkyl group, a trialkylsilyl group, a trialkylsiloxy group, or a sulfonyl group.

Examples of the linear alkyl group include a methyl group, an ethyl group, an n-propyl group, an i-propyl group, an n-butyl group, an i-butyl group, a sec-butyl group, a tert-butyl group, a pentyl group, an i-pentyl group, a neopentyl group, a sec-pentyl group, a 3-pentyl group, a tert-pentyl group, and a hexyl group.

Examples of the cyclic alkyl group include a cyclopentyl group, a cyclohexyl group, a norbornenyl group, and a 1-adamantyl group.

Examples of the alkenyl group include a vinyl group, a 1-propenyl group, a 2-propenyl group (an allyl group), a 2-butenyl group, and a 1,3-butadienyl group.

Examples of the alkynyl group include an ethinyl group, a 1-propynyl group, a 2-propynyl group, and a 2-butynyl group.

Examples of the halogenated alkyl group include a trifluoromethyl group, a 2,2,2-trifluoroethyl group, a 1,1,2,2-tetrafluoroethyl group, a pentafluoroethyl group, a 2,2,3,3,3-pentafluoropropyl group, a 1,1,2,3,3,3-hexafluoropropyl group, and a heptafluoropropyl group.

Examples of the halogenated alkenyl group include a 1-fluorovinyl group and a 2-fluoroallyl group.

Examples of the functional group-containing alkyl group include a cyanomethyl group.

Examples of the saturated heterocyclic group-containing alkyl group include a 3-pyrrolidinopropyl group.

Examples of the aryl group include a phenyl group optionally having an alkyl substituent, an alkoxy substituent, or the like.

Examples of the aralkyl group include a phenylmethyl group and a phenylethyl group.

Examples of the trialkylsilyl group include a trimethylsilyl group.

Examples of the trialkylsiloxy group include a trimethylsiloxy group.

Examples of the sulfonyl group include a fluorosulfonyl group, a trifluoromethane sulfonyl group, and a pentafluoroethane sulfonyl group.

Examples of the di- to hexa-valent heteroatom include an oxygen atom (O), a sulfur atom (S), a nitrogen atom (N), a silicon atom (Si), a phosphorus atom (P), and a boron atom (B). Thereamong, the di- to hexa-valent heteroatom is preferably an oxygen atom, a sulfur atom, or a nitrogen atom.

The "prescribed substituent" refers to —H, —F, a group represented by Formula: $—O_p—(SiR^{11}_2O)_t—SiR^{12}_3$, an alkyl group having from 1 to 7 carbon atoms, an alkenyl group having from 2 to 7 carbon atoms, an alkynyl group having from 2 to 7 carbon atoms, an aryl group having from 6 to 15 carbon atoms, a group represented by $—SO_2X^1$, a group represented by $—SO_3X^2$, or a hydrocarbon group having from 2 to 7 carbon atoms in which $R^1$ and $R^2$ are bound to each other to form a cyclic structure that optionally contains a multiple bond.

In the group represented by Formula: $—O_p—(SiR^{11}_2O)_t—SiR^{12}_3$, the group represented by $—SO_2X^1$, and the group represented by $—SO_3X^2$, the number of carbon atoms of the "alkyl group in which at least one hydrogen atom is optionally substituted with a fluorine atom" is preferably from 1 to 10, more preferably from 1 to 7.

In the group represented by Formula: $—O_p—(SiR^{11}_2O)_t—SiR^{12}_3$, the number of carbon atoms of each of the "alkenyl group in which at least one hydrogen atom is optionally substituted with a fluorine atom" and the "alkynyl group in which at least one hydrogen atom is optionally substituted with a fluorine atom" is preferably from 2 to 10, more preferably from 2 to 7.

In the group represented by Formula: $—O_p—(SiR^{11}_2O)_t—SiR^{12}_3$, the number of carbon atoms of the "aryl group in which at least one hydrogen atom is optionally substituted with a fluorine atom" is preferably from 6 to 8, more preferably from 6 to 7.

In the group represented by Formula: $—O_p—(SiR^{11}_2O)_t—SiR^{12}_3$, "t" is preferably 2,000 or less, more preferably an integer of 0 to 100, still more preferably from 0 to 10.

In the group represented by Formula: $—O_p—(SiR^{11}_2O)_t—SiR^{12}_3$ and the alkyl group having from 1 to 7 carbon atoms, the "alkyl group" may be linear, branched, or cyclic. The "alkyl group" may be a fluoroalkyl group in which a hydrogen atom bound to a carbon atom is substituted with a fluorine atom, or an alkyl group in which a hydrogen atom bound to a carbon atom is substituted with the above-described functional group.

In the group represented by Formula: $—O_p—(SiR^{11}_2O)_t—SiR^{12}_3$ and the alkenyl group having from 2 to 7 carbon atoms, the "alkenyl group" may be linear, branched, or cyclic. The "alkenyl group" may be a fluoroalkenyl group in which a hydrogen atom bound to a carbon atom is substituted with a fluorine atom, or an alkenyl group in which a hydrogen atom bound to a carbon atom is substituted with the above-described functional group.

In the group represented by Formula: $—O_p—(SiR^{11}_2O)_t—SiR^{12}_3$ and the alkynyl group having from 2 to 7 carbon atoms, the "alkynyl group" may be linear, branched, or cyclic. The "alkynyl group" may be a fluoroalkynyl group in which a hydrogen atom bound to a carbon atom is substituted with a fluorine atom, or an alkynyl group in which a hydrogen atom bound to a carbon atom is substituted with the above-described functional group.

In the group represented by Formula: $—O_p—(SiR^{11}_2O)_t—SiR^{12}_3$ and the aryl group having from 6 to 15 carbon, the number of carbon atoms of the "aryl group" is preferably from 6 to 7. The "aryl group" may be a fluoroaryl group in which a hydrogen atom bound to a carbon atom is substituted with a fluorine atom, or an aryl group in which a hydrogen atom bound to a carbon atom is substituted with the above-described functional group.

In the hydrocarbon group having from 2 to 7 carbon atoms in which $R^1$ and $R^2$ are bound to each other to form a cyclic structure that optionally contains a multiple bond, for example, the nitrogen atom (N), $R^1$, and $R^2$ in Formula (I) may form a cyclic amino group or a heteroatom-containing cyclic amino group. In these groups, at least one hydrogen atom bound to a carbon atom may be substituted with a fluorine atom, or a hydrogen atom bound to a carbon atom may be substituted with the above-described functional group. These groups may contain a double bond or a triple bond in their cyclic structures.

Examples of the cyclic amino group include a pyrrolidino group and a piperidino group.

Examples of the heteroatom-containing cyclic amino group include a 4-morpholino group, a succinimidyl group, and a maleimidyl group, which contain a heteroatom.

Among the above-described groups, $R^1$ and $R^2$ are each preferably a linear alkyl group, a halogenated alkyl group, or a functional group-containing alkyl group.

Examples of the nitrogen-containing lithium salt compound (I) include compounds represented by the following formulae:

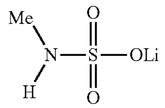
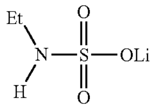
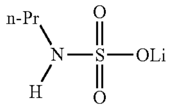
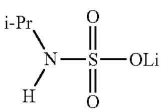
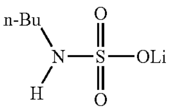
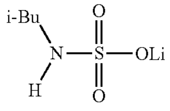
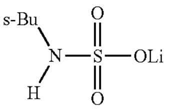
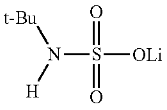
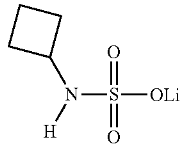
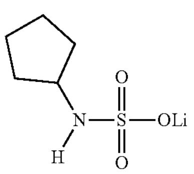
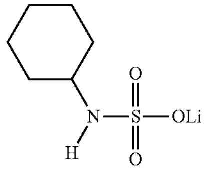

-continued

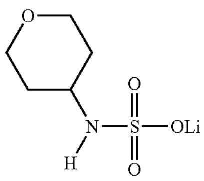
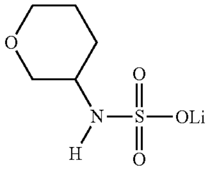
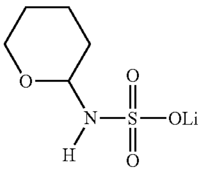
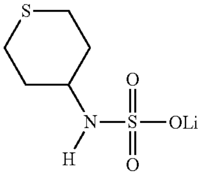
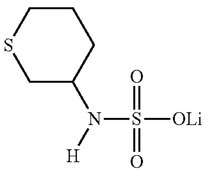
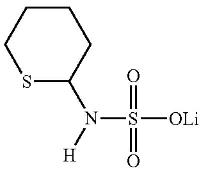
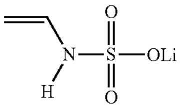
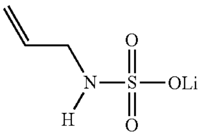
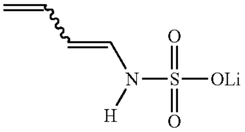
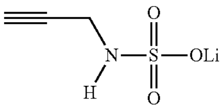
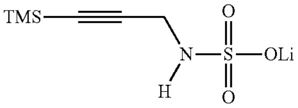
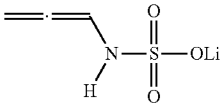
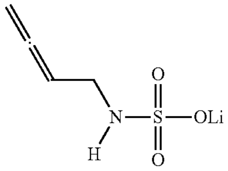
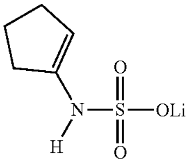
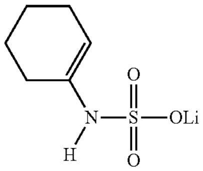
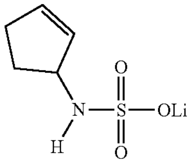
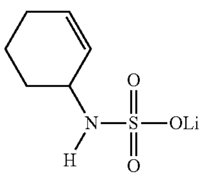
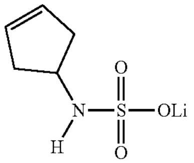
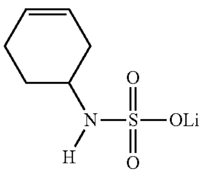
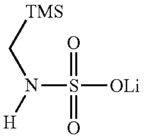
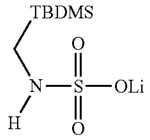

-continued
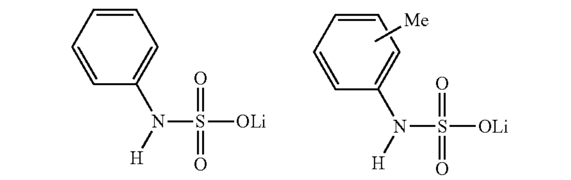
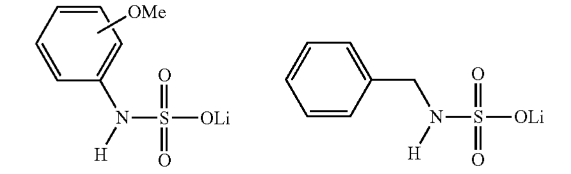
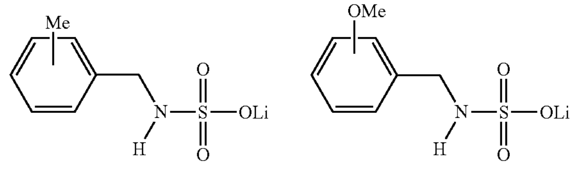
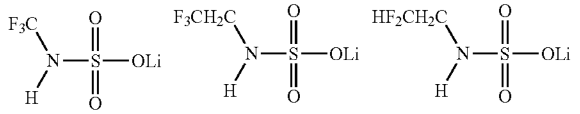
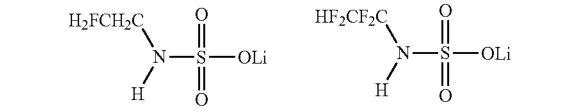
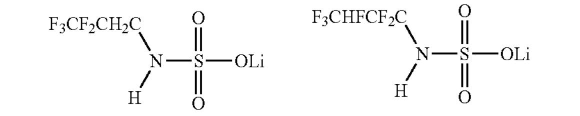
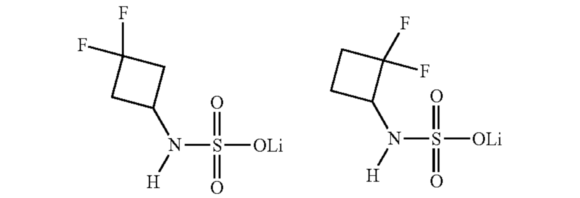
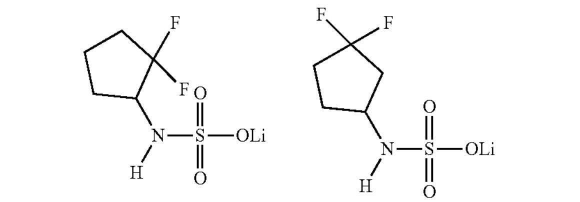
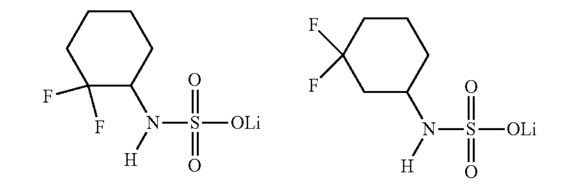
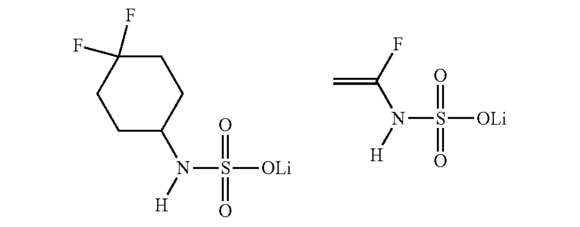
-continued
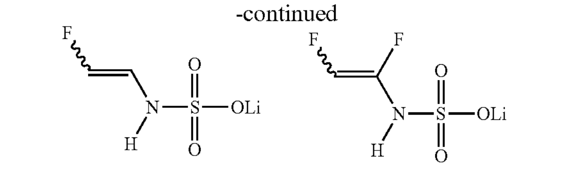
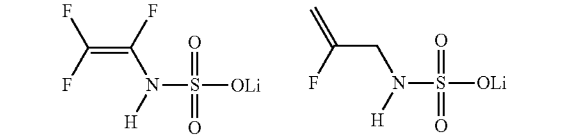
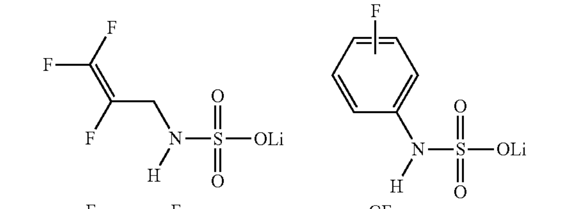
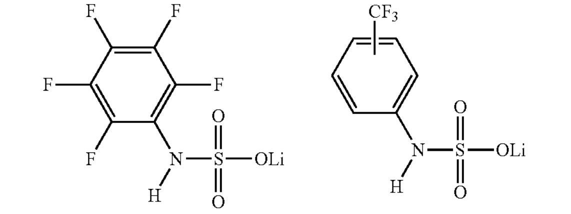
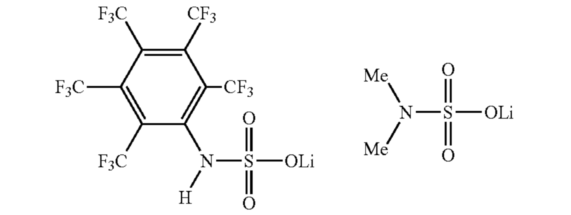
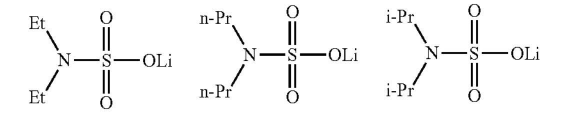
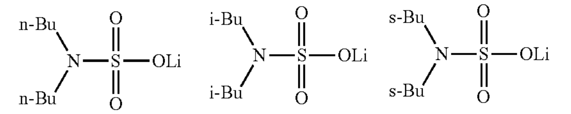
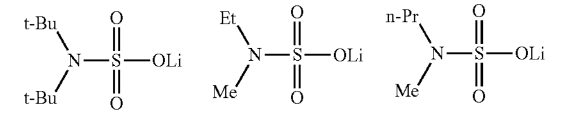
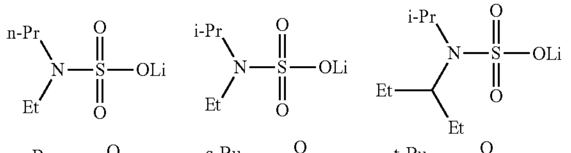
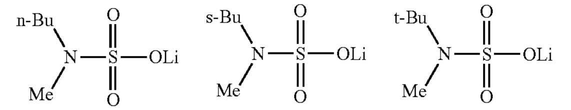
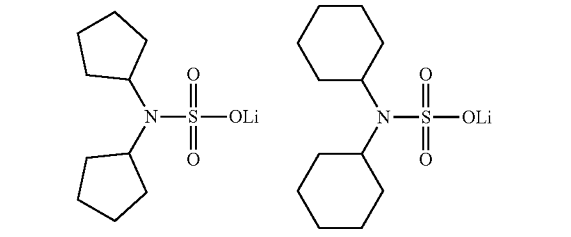

-continued
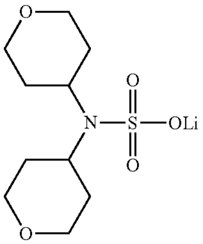
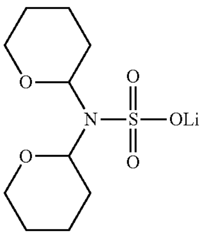
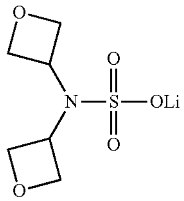
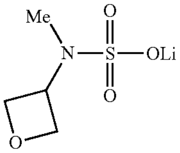
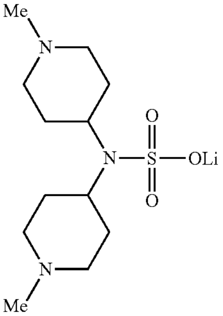
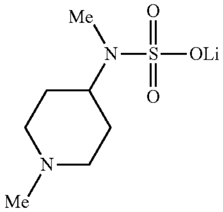
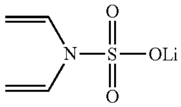
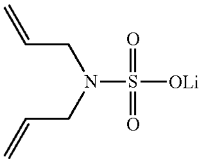
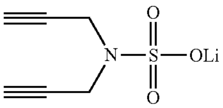
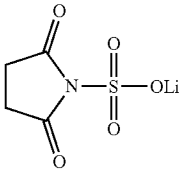
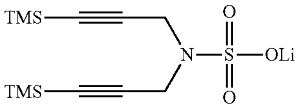
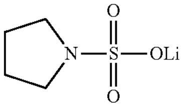
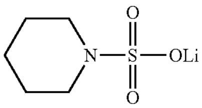
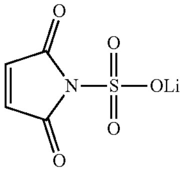
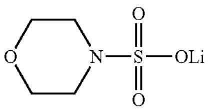
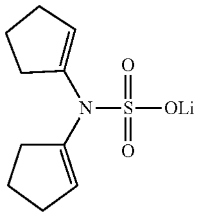
-continued
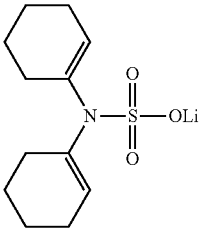
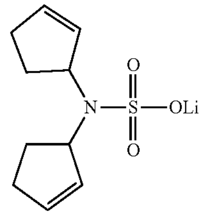
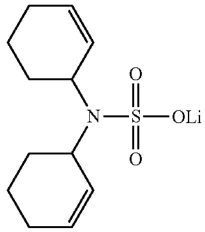
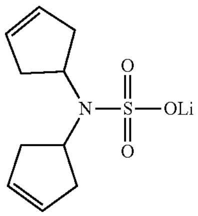
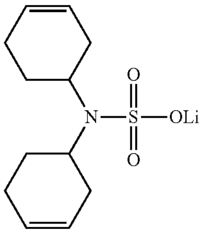
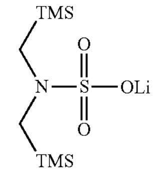
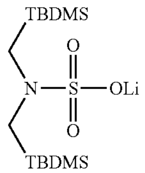
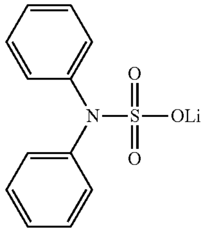
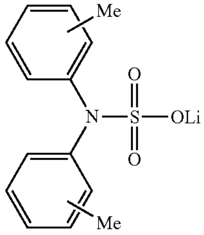
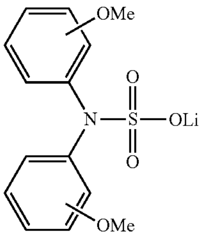
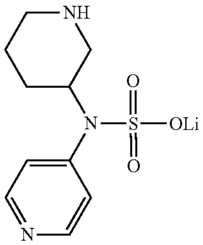
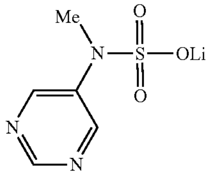

-continued
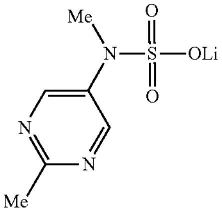
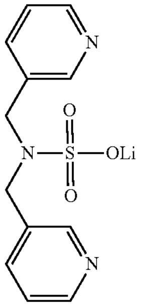
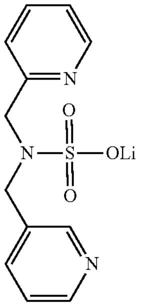
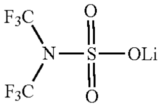
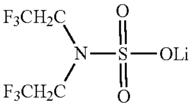
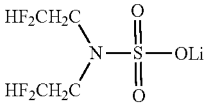
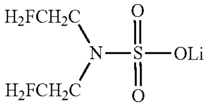
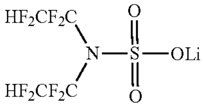
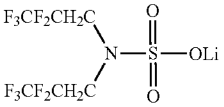
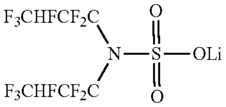
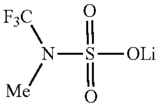
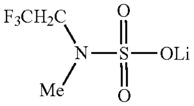
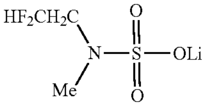
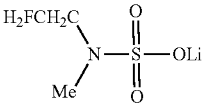
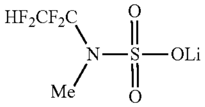
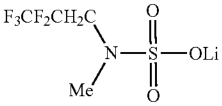
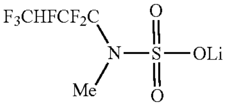
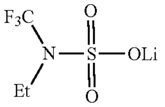
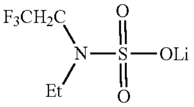
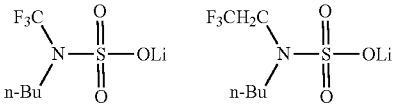
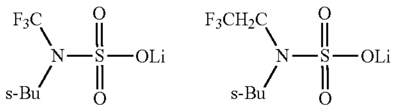
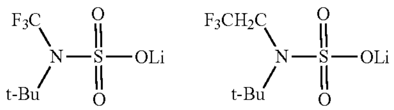
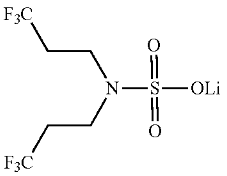
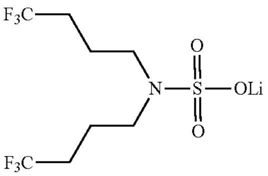
-continued
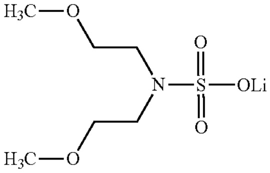
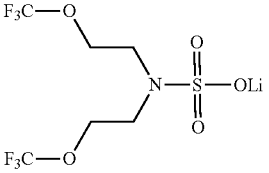
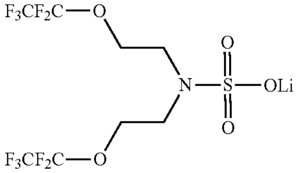
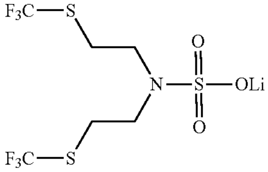
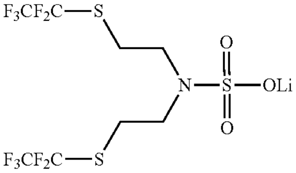
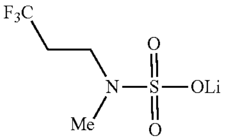
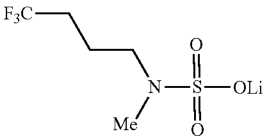
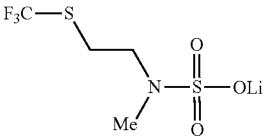
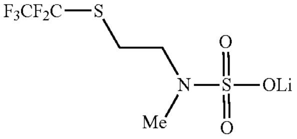
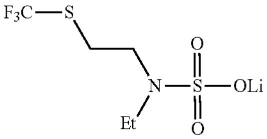
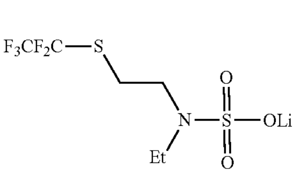
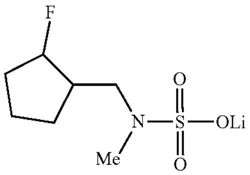
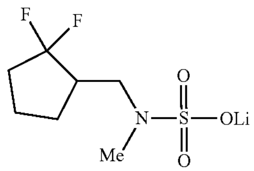
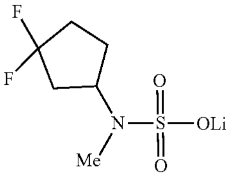
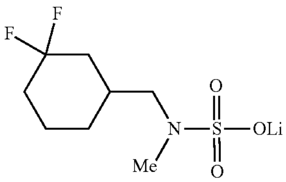
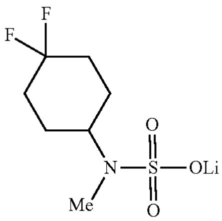

-continued

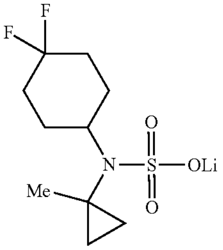
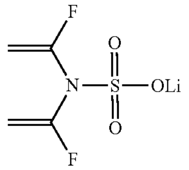
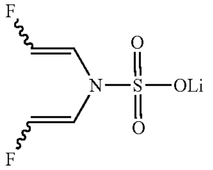
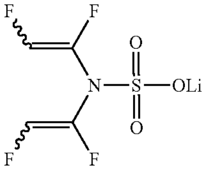
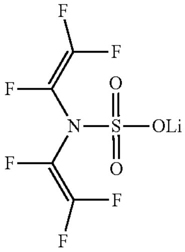
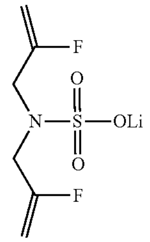
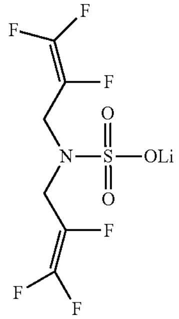
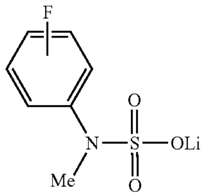
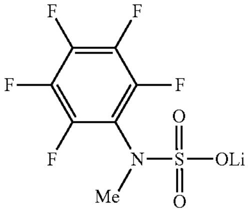
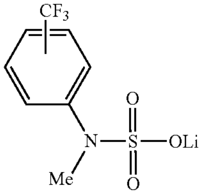
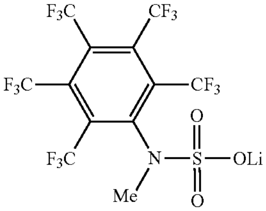
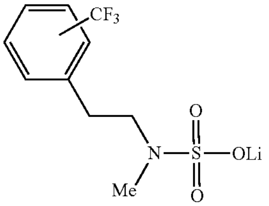
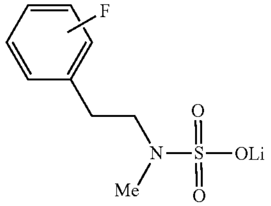
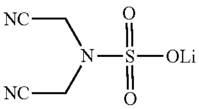
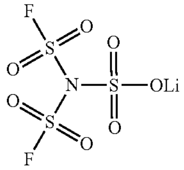
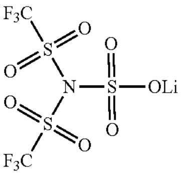
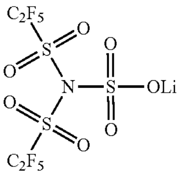

-continued

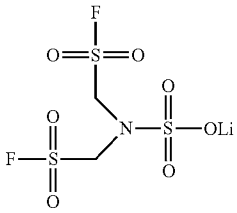
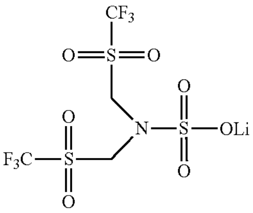
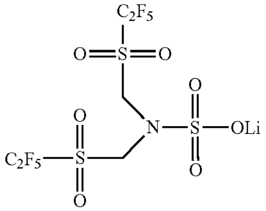
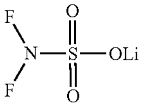
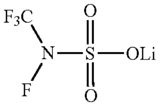
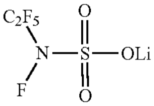
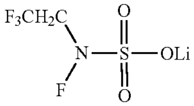
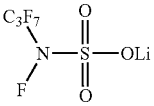

It is noted here that, in the present specification, Me, Et, n-Pr, i-Pr, n-Bu, and i-Bu, s-Bu, t-Bu, TMS, and TBDMS represent a methyl group, an ethyl group, an n-propyl group, an iso-propyl group, an n-butyl group, an iso-butyl group, a sec-butyl group, a tert-butyl group, a trimethylsilyl group, and a tert-butyldimethylsilyl group, respectively. In the case of the following formula, R may be bound to any of the carbon atoms constituting the benzene ring and, for example, R may be bound at any of the o-, m-, and p-positions.

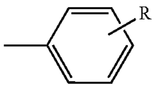

Those compounds exemplified in the present specification include their geometric isomers (if any) and are not limited to the described specific examples.

Thereamong, as the nitrogen-containing lithium salt compound (I), for example, compounds represented by the following formulae are preferred.

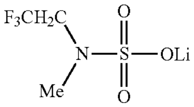
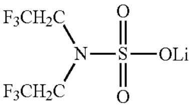
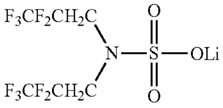
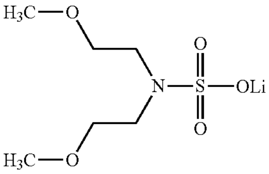

-continued

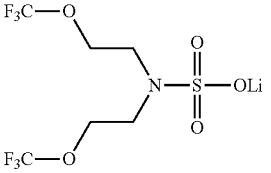

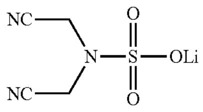

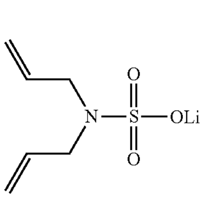

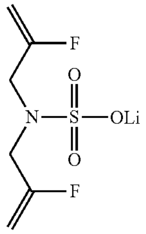

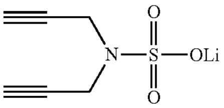

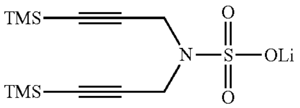

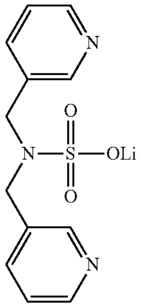

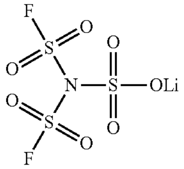

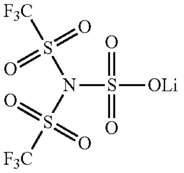

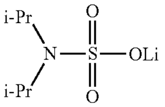

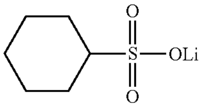

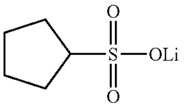

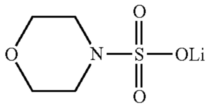

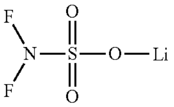

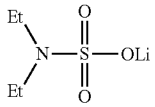

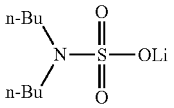

Among these compounds preferred as the nitrogen-containing lithium salt compound (I), the nitrogen-containing lithium salt compound (I) is more preferably any of lithium diethylsulfamate (I-1), Compound (I-2), and Compound (I-3), which are represented by the following respective Formulae, still more preferably lithium diethylsulfamate (I-1) represented by Formula (I-1).

(I-1)

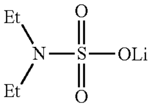

(I-2)

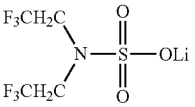

(I-3)

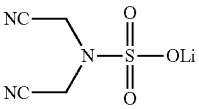

The nonaqueous electrolyte solution may contain the nitrogen-containing lithium salt compound (I) singly, or in combination of two or more kinds thereof.

An upper limit of a content of the nitrogen-containing lithium salt compound (I) is preferably 5.0% by mass or less, more preferably 3.0% by mass or less, still more preferably 2.0% by mass or less, with respect to a total amount of the nonaqueous electrolyte solution. As long as the upper limit of the content of the nitrogen-containing lithium salt compound (I) is in this range, the battery characteristics such as the capacity value and the resistance value can be improved in a well-balanced manner.

A lower limit of the content of the nitrogen-containing lithium salt compound (I) is preferably 0.001% by mass or more, more preferably 0.005% by mass or more, still more preferably 0.010% by mass or more, particularly preferably 0.1% by mass or more, with respect to a total amount of the nonaqueous electrolyte solution. As long as the lower limit of the content of the nitrogen-containing lithium salt compound (I) is in this range, an SEI film and the like derived from the nitrogen-containing lithium salt compound (I) are formed in a sufficient amount, so that the battery characteristics after a durability test can be improved.

<Cyclic Sulfur-Containing Ester Compound (II)>

Next, the cyclic sulfur-containing ester compound (II) will be described.

The cyclic sulfur-containing ester compound (II) is a compound represented the following Formula (II).

(II)

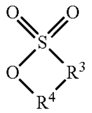

In Formula (II):

$R^3$ represents an oxygen atom, an alkylene group having from 2 to 6 carbon atoms, or an alkenylene group having from 2 to 6 carbon atoms, $R^4$ represents an alkylene group having from 2 to 6 carbon atoms, an alkenylene group having from 2 to 6 carbon atoms, a group represented by the following Formula (ii-1), or a group represented by the following Formula (ii-2), and

* represents a binding position, (ii-1)

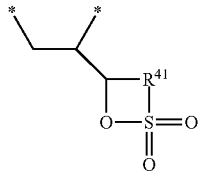

(ii-2)

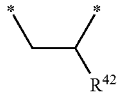

wherein, in Formula (ii-1), $R^{41}$ represents an oxygen atom, an alkylene group having from 1 to 6 carbon atoms, an alkenylene group having from 2 to 6 carbon atoms, or an oxymethylene group, and wherein, in Formula (ii-2), $R^{42}$ represents an alkyl group having from 1 to 6 carbon atoms, or an alkenyl group having from 2 to 6 carbon atoms.

In Formula (II), $R^3$ is preferably an alkylene group having from 2 to 3 carbon atoms, a vinylene group, or an oxygen atom, more preferably a trimethylene group, a vinylene group, or an oxygen atom, particularly preferably an oxygen atom.

In the cyclic sulfur-containing ester compound (II), $R^3$ is preferably an oxygen atom. This makes a thermally and chemically stable inorganic salt structure more likely to be formed. Therefore, in a high-temperature environment, for example, elution of a component of the SEI film and the like and modification of the SEI film and the like, which impair the durability of the SEI film and the like, are unlikely to occur. As a result, the durability of the SEI film and the like, as well as the battery characteristics of a lithium secondary battery are improved.

In Formula (II), $R^4$ is preferably a group represented by Formula (ii-1) or a group represented by Formula (ii-2).

In Formula (ii-1), $R^{41}$ is preferably an alkylene group having from 1 to 3 carbon atoms, an alkenylene group having from 1 to 3 carbon atoms, or an oxymethylene group, more preferably an oxymethylene group.

In Formula (ii-2), $R^{42}$ is preferably an alkyl group having from 1 to 3 carbon atoms or an alkenyl group having from 2 to 3 carbon atoms, more preferably a propyl group.

Specific examples of the cyclic sulfur-containing ester compound (II) include compounds represented by Formulae (II-1) and (IIa-1) to (IIa-4).

Hereinafter, the compound represented by Formula (IIa-1) may be referred to as "cyclic sulfur-containing ester compound (IIa-1)", and the compound represented by Formula (IIa-2) may be referred to as "cyclic sulfur-containing ester compound (IIa-2)".

(II-1)

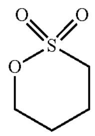

-continued (IIa-1)

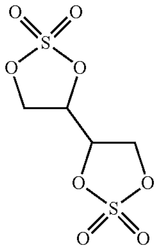

(IIa-2)

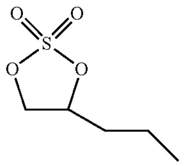

(IIa-3)

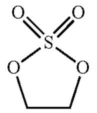

(IIa-4)

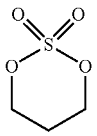

The nonaqueous electrolyte solution may contain the cyclic sulfur-containing ester compound (II) singly, or in combination of two or more kinds thereof.

An upper limit of a content of the cyclic sulfur-containing ester compound (II) is preferably 5.0% by mass or less, more preferably 3.0% by mass or less, still more preferably 2.0% by mass or less, with respect to a total amount of the nonaqueous electrolyte solution. As long as the upper limit of the content of the cyclic sulfur-containing ester compound (II) is in this range, a lithium secondary battery can be operated without deterioration of the lithium ion conductivity caused by the SEI film and the like. In addition, with the SEI film and the like containing a sulfite or sulfate structure, the battery characteristics of the lithium secondary battery are improved.

A lower limit of the content of the cyclic sulfur-containing ester compound (II) is preferably 0.01% by mass or more, more preferably 0.05% by mass or more, still more preferably 0.10% by mass or more, with respect to a total amount of the nonaqueous electrolyte solution. As long as the lower limit of the content of the cyclic sulfur-containing ester compound (II) is in this range, the SEI film and the like contain a sufficient amount of a sulfite or sulfate structure. This makes a thermally and chemically stable inorganic salt or polymer structure more likely to be formed. Therefore, in a high-temperature environment, for example, elution of a component of the SEI film and the like and modification of the SEI film and the like, which impair the durability of the SEI film and the like, are unlikely to occur. As a result, the durability of the SEI film and the like, as well as the battery characteristics of the lithium secondary battery are improved.

When the nonaqueous electrolyte solution contains the cyclic sulfur-containing ester compound (IIa-1), the content thereof is preferably in the below-described range.

An upper limit of the content of the cyclic sulfur-containing ester compound (IIa-1) is preferably 5.0% by mass or less, more preferably 3.0% by mass or less, still more preferably 2.0% by mass or less, with respect to a total amount of the nonaqueous electrolyte solution. As long as the upper limit of the content of the cyclic sulfur-containing ester compound (IIa-1) is in this range, a lithium secondary battery can be operated without deterioration of the lithium cation conductivity caused by the SEI film and the like. In addition, with the SEI film and the like containing a sulfate structure, the battery characteristics of the lithium secondary battery are improved.

A lower limit of the content of the cyclic sulfur-containing ester compound (IIa-1) is preferably 0.01% by mass or more, more preferably 0.05% by mass or more, still more preferably 0.10% by mass or more, with respect to a total amount of the nonaqueous electrolyte solution. As long as the lower limit of the content of the cyclic sulfur-containing ester compound (IIa-1) is in this range, the SEI film and the like contain a sufficient amount of a structure mainly composed of a sulfate. This makes a thermally and chemically stable inorganic salt or polymer structure more likely to be formed. Therefore, in a high-temperature environment, for example, elution of a component of the SEI film and the like and modification of the SEI film and the like, which impair the durability of the SEI film and the like, are unlikely to occur. As a result, the durability of the SEI film and the like, as well as the characteristics of the lithium secondary battery after high-temperature storage are improved.

When the nonaqueous electrolyte solution contains the cyclic sulfur-containing ester compound (IIa-2), the content thereof is preferably in the below-described range.

An upper limit of the content of the cyclic sulfur-containing ester compound (IIa-2) is preferably 5.0% by mass or less, more preferably 3.0% by mass or less, still more preferably 2.0% by mass or less, with respect to a total amount of the nonaqueous electrolyte solution. As long as the upper limit of the content of the cyclic sulfur-containing ester compound (IIa-2) is in this range, a lithium secondary battery can be operated without deterioration of the lithium cation conductivity caused by the SEI film and the like. In addition, with the SEI film and the like containing a sulfate structure, the battery characteristics of the lithium secondary battery are improved.

A lower limit of the content of the cyclic sulfur-containing ester compound (IIa-2) is preferably 0.01% by mass or more, more preferably 0.05% by mass or more, still more preferably 0.10% by mass or more, with respect to a total amount of the nonaqueous electrolyte solution. As long as the lower limit of the content of the cyclic sulfur-containing ester compound (IIa-2) is in this range, the SEI film and the like contain a sufficient amount of a structure mainly composed of a sulfate. This makes a thermally and chemically stable inorganic salt or polymer structure more likely to be formed. Therefore, in a high-temperature environment, for example, elution of a component of the SEI film and the like and modification of the SEI film and the like, which impair the durability of the SEI film and the like, are unlikely to occur. As a result, the durability of the SEI film and the like, as well as the characteristics of the lithium secondary battery after high-temperature storage are improved.

(Cyclic Dicarbonyl Compound (III))

The cyclic dicarbonyl compound (III) is a compound represented by Formula (III).

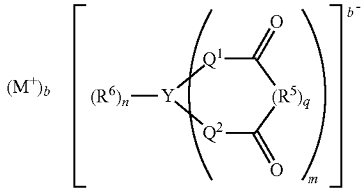

(III)

In Formula (III):

M represents an alkali metal,

Y represents a transition element, or an element of Group 13, 14, or 15 of the periodic table, b represents an integer from 1 to 3, m represents an integer from 1 to 4, n represents an integer from 0 to 8, q represents 0 or 1, $R^5$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, the halogenated alkylene group, the arylene group and the halogenated arylene group each optionally containing a substituent or a heteroatom in structure thereof and, when q is 1 and m is from 2 to 4, m instances of $R^5$ are optionally bound to each other, $R^6$ represents a halogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, the halogenated alkyl group, the aryl group and the halogenated aryl group each optionally containing a substituent or a heteroatom in a structure thereof and, when n is from 2 to 8, n instances of $R^6$ are optionally bound to each other to form a ring, and each of $Q^1$ and $Q^2$ independently represents an oxygen atom or a carbon atom.

M represents an alkali metal. Examples of the alkali metal include lithium, sodium, and potassium. Thereamong, M is preferably lithium.

Y represents a transition element, or an element of Group 13, 14, or 15 of the periodic table. Y is preferably Al, B, V, Ti, Si, Zr, Ge, Sn, Cu, Y, Zn, Ga, Nb, Ta, Bi, P, As, Sc, Hf, or Sb, more preferably Al, B, or P. When Y is Al, B, or P, an anionic compound is synthesized relatively easily, so that the production cost can be reduced.

Further, b represents the valence of an anion or the number of cations, which is an integer of 1 to 3, preferably 1. When b is 3 or less, a salt of an anionic compound can be easily dissolved in a mixed organic solvent.

Each of m and n represents a value relating to the number of ligands, and is determined based on the type of M. The value of m is an integer of 1 to 4, and the value of n is an integer of 0 to 8.

Moreover, q represents 0 or 1. When q is 0, the chelate ring is a five-membered ring, while when q is 1, the chelate ring is a six-membered ring.

$R^5$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms. These alkylene group, halogenated alkylene group, arylene group, and halogenated arylene group may each contain a substituent or a heteroatom in their structures. Specifically, $R^5$ may contain a substituent in place of a hydrogen atom of any of these groups. Examples of the substituent include a halogen atom, a linear or cyclic alkyl group, an aryl group, an alkenyl group, an alkoxy group, an aryloxy group, a sulfonyl group, an amino group, a cyano group, a carbonyl group, an acyl group, an amide group, and a hydroxy group. $R^5$ may have a structure in which a nitrogen atom, a sulfur atom, or an oxygen atom is introduced in place of a carbon atom of any of these groups. When q is 1 and m is from 2 to 4, m $R^5$s may be bound to each other. Examples of such a case include ligands such as ethylenediaminetetraacetic acid.

$R^6$ represents a halogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms. These alkyl group, halogenated alkyl group, aryl group, and halogenated aryl group, similarly to the case of $R^5$, may each contain a substituent or a heteroatom in their structures and, when n is from 2 to 8, n $R^6$s may be bound to each other to form a ring. $R^6$ is preferably an electron-withdrawing group, particularly preferably a fluorine atom.

Each of $Q^1$ and $Q^2$ independently represents O or C. In other words, a ligand is bonded to Y via these heteroatoms.

Specific examples of the cyclic dicarbonyl compound (III) include compounds represented by the following Formulae (III-1) and (III-2).

The compound represented by Formula (III-1) may be hereinafter referred to as "lithium bis(oxalato)borate (III-1)".

(III-1)

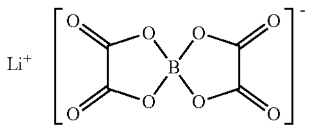

(III-2)

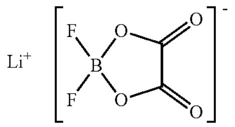

When the nonaqueous electrolyte solution contains the cyclic dicarbonyl compound (III), a content thereof is preferably in the below-described range.

An upper limit of the content of the cyclic dicarbonyl compound (III) is preferably 10% by mass or less, more preferably 5.0% by mass or less, still more preferably 3.0% by mass or less, particularly preferably 2.0% by mass or less, with respect to a total amount of the nonaqueous electrolyte solution. As long as the upper limit of the content of the cyclic dicarbonyl compound (III) is in this range, a lithium secondary battery can be operated without deterioration of the lithium cation conductivity caused by the SEI film and the like. In addition, with the SEI film and the like containing boric acid structure, the battery characteristics of the lithium secondary battery are improved.

A lower limit of the content of the cyclic dicarbonyl compound (III) is preferably 0.01% by mass or more, more preferably 0.05% by mass or more, still more preferably 0.10% by mass or more, with respect to a total amount of the nonaqueous electrolyte solution. As long as the lower limit of the content of the cyclic dicarbonyl compound (III) is in this range, the SEI film and the like contain a sufficient amount of a structure mainly composed of a boric acid. This makes a thermally and chemically stable inorganic salt or polymer structure more likely to be formed. Therefore, in a high-temperature environment, for example, elution of a component of the SEI film and the like and modification of the SEI film and the like, which impair the durability of the SEI film and the like, are unlikely to occur. As a result, the durability of the SEI film and the like, as well as the characteristics of the lithium secondary battery after high-temperature storage are improved.

(Cyclic Carbonate Compound (IV))

The cyclic carbonate compound (IV) is represented by Formula (IV).

(IV)

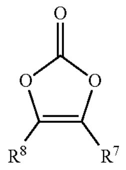

In Formula (IV), each of $R^7$ and $R^8$ independently represents a hydrogen atom, a methyl group, an ethyl group, or a propyl group.

Specific examples of the cyclic carbonate compound (IV) include compounds represented by the following Formulae (IV-1) to (IV-7).

The compound represented by Formula (IV-1) may be hereinafter referred to as "vinylene carbonate (IV-1)".

(IV-1)

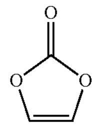

(IV-2)

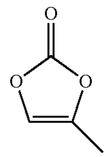

(IV-3)

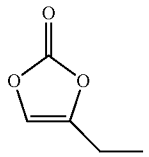

(IV-4)

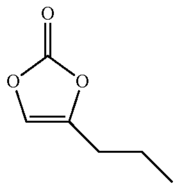

-continued (IV-5)

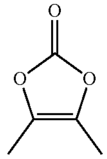

(IV-6)

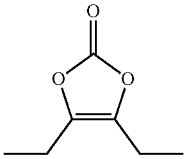

(IV-7)

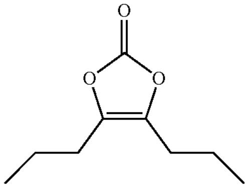

When the nonaqueous electrolyte solution contains the cyclic carbonate compound (IV), a content thereof is preferably in the below-described range.

An upper limit of the content of the cyclic carbonate compound (IV) is preferably 10.0% by mass or less, more preferably 5.0% by mass or less, still more preferably 3.0% by mass or less, with respect to a total amount of the nonaqueous electrolyte solution. As long as the upper limit of the content of the cyclic carbonate compound (IV) is in this range, an increase in the thickness of SEI film and the like can be inhibited while inhibiting the decomposition of a nonaqueous solvent on a positive electrode or a negative electrode. The nonaqueous solvent will be described below. As a result, the characteristics of a lithium secondary battery after high-temperature storage are improved.

A lower limit of the content of the cyclic carbonate compound (IV) is preferably 0.10% by mass or more, more preferably 0.20% by mass or more, still more preferably 0.30% by mass or more, with respect to a total amount of the nonaqueous electrolyte solution. As long as the lower limit of the content of the cyclic carbonate compound (IV) is in this range, an SEI film and the like are formed at a thickness that enables to inhibit the decomposition of a nonaqueous solvent contained in the nonaqueous electrolyte solution. As a result, the characteristics of a lithium secondary battery after high-temperature storage are improved.

When the nonaqueous electrolyte solution contains the vinylene carbonate (IV-1), the content thereof is preferably in the below-described range.

An upper limit of the content of the vinylene carbonate (IV-1) is preferably 10.0% by mass or less, more preferably 5.0% by mass or less, still more preferably 3.0% by mass or less, particularly preferably 2.0% by mass or less, with respect to a total amount of the nonaqueous electrolyte solution. As long as the upper limit of the content of the vinylene carbonate (IV-1) is in this range, an increase in the thickness of SEI film and the like can be inhibited while inhibiting the decomposition of a nonaqueous solvent on a positive electrode or a negative electrode. As a result, the characteristics of a lithium secondary battery after high-temperature storage are improved.

A lower limit of the content of the vinylene carbonate (IV-1) is preferably 0.10% by mass or more, more preferably 0.20% by mass or more, still more preferably 0.30% by mass or more, with respect to a total amount of the nonaqueous electrolyte solution. As long as the lower limit of the content of the vinylene carbonate (IV-1) is in this range, an SEI film and the like are formed at a thickness that enables to inhibit the decomposition of a nonaqueous solvent contained in the nonaqueous electrolyte solution. As a result, the characteristics of a lithium secondary battery after high-temperature storage are improved.

<Nonaqueous Solvent>

The nonaqueous electrolyte solution generally contains a nonaqueous solvent. The nonaqueous solvent can be selected as appropriate from various known solvents. The nonaqueous solvent may be contained singly, or in combination of two or more kinds thereof.

Examples of the nonaqueous solvent include cyclic carbonates, fluorine-containing cyclic carbonates, chain carbonates, fluorine-containing chain carbonates, aliphatic carboxylic acid esters, fluorine-containing aliphatic carboxylic acid esters, γ-lactones, fluorine-containing γ-lactones, cyclic ethers, fluorine-containing cyclic ethers, chain ethers, fluorine-containing chain ethers, nitriles, amides, lactams, nitromethane, nitroethane, sulfolane, trimethyl phosphate, dimethyl sulfoxide, and dimethyl sulfoxide phosphate.

Examples of the cyclic carbonates include ethylene carbonate (EC), propylene carbonate (PC), and butylene carbonate (BC).

Examples of the fluorine-containing cyclic carbonates include fluoroethylene carbonate (FEC), difluoroethylene carbonate (DFEC), and trifluoropropylene carbonate.

Examples of the chain carbonates include dimethyl carbonate (DMC), diethyl carbonate (DEC), ethyl methyl carbonate (EMC), methyl propyl carbonate (MPC), ethyl propyl carbonate (EPC), and dipropyl carbonate (DPC).

Examples of the fluorine-containing chain carbonates include methyl 2,2,2-trifluoroethyl carbonate.

Examples of the aliphatic carboxylic acid esters include methyl formate, methyl acetate, methyl propionate, methyl butyrate, methyl isobutyrate, methyl trimethylbutyrate, ethyl formate, ethyl acetate, ethyl propionate, ethyl butyrate, ethyl isobutyrate, and ethyl trimethylbutyrate.

Examples of the fluorine-containing aliphatic carboxylic acid esters include methyl difluoroacetate, methyl 3,3,3-trifluoropropionate, ethyl difluoroacetate, and 2,2,2-trifluoroethyl acetate.

Examples of the γ-lactones include γ-butyrolactone and γ-valerolactone.

Examples of the cyclic ethers include tetrahydrofuran, 2-methyltetrahydrofuran, tetrahydropyran, 1,3-dioxolane, 4-methyl-1,3-dioxolane, 1,3-dioxane, and 1,4-dioxane.

Examples of the chain ethers include 1,2-ethoxyethane (DEE), ethoxymethoxyethane (EME), diethyl ether, 1,2-dimethoxyethane, and 1,2-dibutoxyethane.

Examples of the fluorine-containing chain ethers include $HCF_2CF_2CH_2OCF_2CF_2H$, $CF_3CF_2CH_2OCF_2CF_2H$, $HCF_2CF_2CH_2OCF_2CFHCF_3$, $CF_3CF_2CH_2OCF_2CFHCF_3$, $C_6F_{13}OCH_3$, $C_6F_{13}OC_2H_5$, $C_8F_{17}OCH_3$, $C_8F_{17}OC_2H_5$, $CF_3CFHCF_2CH(CH_3)OCF_2CFHCF_3$, $HCF_2CF_2OCH(C_2H_5)_2$, $HCF_2CF_2OC_4H_9$, $HCF_2CF_2OCH_2CH(C_2H_5)_2$, and $HCF_2CF_2OCH_2CH(CH_3)_2$.

Examples of the nitriles include acetonitrile, glutaronitrile, adiponitrile, methoxyacetonitrile, and 3-methoxypropionitrile.

Examples of the amides include N,N-dimethylformamide.

Examples of the lactams include N-methylpyrrolidinone, N-methyloxazolidinone, and N,N'-dimethylimidazolidinone.

The nonaqueous solvent preferably contains at least one selected from the group consisting of cyclic carbonates, fluorine-containing cyclic carbonates, chain carbonates, and fluorine-containing chain carbonates. In this case, a total ratio of the cyclic carbonates, the fluorine-containing cyclic carbonates, the chain carbonates, and the fluorine-containing chain carbonates is preferably from 50% by mass to 100% by mass, more preferably from 60% by mass to 100% by mass, still more preferably from 80% by mass to 100% by mass, with respect to a total amount of the nonaqueous solvent.

The nonaqueous solvent preferably contains at least one selected from the group consisting of cyclic carbonates and chain carbonates. In this case, a total ratio of the cyclic carbonates and the chain carbonates in the nonaqueous solvent is preferably from 50% by mass to 100% by mass, more preferably from 60% by mass to 100% by mass, still more preferably from 80% by mass to 100% by mass, with respect to a total amount of the nonaqueous solvent.

An upper limit of the content of the nonaqueous solvent is preferably 99% by mass or less, more preferably 97% by mass or less, still more preferably 90% by mass or less, with respect to a total amount of the nonaqueous electrolyte solution.

A lower limit of the content of the nonaqueous solvent is preferably 60% by mass or more, more preferably 70% by mass or more, with respect to a total amount of the nonaqueous electrolyte solution.

From the standpoint of further improving the dissociation of an electrolyte and the ion mobility, the nonaqueous solvent preferably has an intrinsic viscosity of 10.0 mPa's or less at 25° C.

<Electrolyte>

The nonaqueous electrolyte solution generally contains an electrolyte.

The electrolyte preferably contains at least one of a lithium salt containing fluorine (hereinafter, may be referred to as "fluorine-containing lithium salt") or a lithium salt not containing fluorine.

Examples of the fluorine-containing lithium salt include inorganic acid anion salts and organic acid anion salts.

Examples of the inorganic acid anion salts include lithium hexafluorophosphate ($LiPF_6$), lithium tetrafluoroborate ($LiBF_4$), lithium hexafluoroarsenate ($LiAsF_6$), and lithium hexafluorotantalate ($LiTaF_6$).

Examples of the organic acid anion salts include lithium trifluoromethane sulfonate ($LiCF_3SO_3$), lithium bis(trifluoromethanesulfonyl)imide ($Li(CF_3SO_2)_2N$), and lithium bis (pentafluoroethanesulfonyl)imide ($Li(C_2FsSO_2)_2N$). Thereamong, the fluorine-containing lithium salt is particularly preferably $LiPF_6$.

Examples of the lithium salt not containing fluorine include lithium perchlorate ($LiClO_4$), lithium tetrachloroaluminate ($LiAlCl_4$), and lithium decachlorodecaborate ($Li_2B_{10}Cl_{10}$).

When the electrolyte contains a fluorine-containing lithium salt, a content ratio of the fluorine-containing lithium salt is preferably from 50% by mass to 100% by mass, more preferably from 60% by mass to 100% by mass, still more preferably from 80% by mass to 100% by mass or less, with respect to a total amount of the electrolyte.

When the fluorine-containing lithium salt contains lithium hexafluorophosphate ($LiPF_6$), the content ratio of lithium hexafluorophosphate ($LiPF_6$) is preferably from 50% by mass to 100% by mass, more preferably from 60% by mass to 100% by mass, still more preferably from 80% by mass to 100% by mass or less, with respect to a total amount of the electrolyte.

When the nonaqueous electrolyte solution contains an electrolyte, the concentration of the electrolyte in the nonaqueous electrolyte solution is preferably from 0.1 mol/L to 3 mol/L, more preferably from 0.5 mol/L to 2 mol/L.

When the nonaqueous electrolyte solution contains lithium hexafluorophosphate ($LiPF_6$), the concentration of lithium hexafluorophosphate ($LiPF_6$) in the nonaqueous electrolyte solution is preferably from 0.1 mol/L to 3 mol/L, more preferably from 0.5 mol/L to 2 mol/L.

<Other Components>

The nonaqueous electrolyte solution may also contain other components if necessary.

Examples of the other components include acid anhydrides.

[Lithium Secondary Battery Precursor]

Next, the lithium secondary battery precursor according to one embodiment of the disclosure will be described.

The lithium secondary battery precursor according to the present embodiment includes a positive electrode, a negative electrode, and an electrolyte solution. The positive electrode is capable of occluding and releasing lithium ions. The negative electrode is also capable of occluding and releasing lithium ions. The electrolyte solution is the nonaqueous electrolyte solution according to the present embodiment.

The lithium secondary battery precursor according to the present embodiment may further include a casing and a separator, in addition to the positive electrode, the negative electrode, and the electrolyte solution. The casing houses the positive electrode, the negative electrode, the separator, and the electrolyte solution.

A case where the lithium secondary battery precursor includes the positive electrode, the negative electrode, the electrolyte solution, the casing, and the separator will now be described.

The lithium secondary battery precursor represents a lithium secondary battery that has not yet been subjected to charging or discharging. In other words, in the lithium secondary battery precursor, the negative electrode does not include an SEI film, and the positive electrode does not include a CEI film.

<Casing>

The shape and the like of the casing are not particularly limited, and are selected as appropriate in accordance with the intended use and the like of the lithium secondary battery precursor according to the present embodiment. Examples of the casing include a casing that includes a laminated film, and a casing composed of a battery can and a battery can lid.

<Positive Electrode>

The positive electrode preferably contains at least one positive electrode active material. The positive electrode active material is capable of occluding and releasing lithium ions.

The positive electrode according to the present embodiment includes a positive electrode current collector and a positive electrode mixture layer. The positive electrode mixture layer is arranged on at least a portion of the surface of the positive electrode current collector.

A material of the positive electrode current collector is, for example, a metal or an alloy. More particularly, examples of the material of the positive electrode current collector include aluminum, nickel, stainless steel (SUS), and copper. Thereamong, from the standpoint of the balance between the degree of conductivity and the cost, the material of the positive electrode current collector is preferably aluminum.

The term "aluminum" used herein means pure aluminum or an aluminum alloy. The positive electrode current collector is preferably an aluminum foil. A material of the aluminum foil is not particularly limited, and examples thereof include A1085 and A3003.

The positive electrode mixture layer contains a positive electrode active material and a binder.

The positive electrode active material is not particularly limited as long as it is a substance capable of occluding and releasing lithium ions, and may be adjusted as appropriate in accordance with the intended use and the like of the lithium secondary battery precursor.

Examples of the positive electrode active material include a first oxide and a second oxide.

The first oxide contains lithium (Li) and nickel (Ni) as constituent metal elements.

The second oxide contains Li, Ni, and at least one metal element other than Li and Ni as constituent metal elements. Examples of the metal element other than Li and Ni include transition metal elements and main-group metal elements. The second oxide contains the metal element other than Li and Ni preferably at a ratio equivalent to or lower than that of Ni in terms of the number of atoms. The metal element other than Li and Ni may be, for example, at least one selected from the group consisting of Co, Mn, Al, Cr, Fe, V, Mg, Ca, Na, Ti, Zr, Nb, Mo, W, Cu, Zn, Ga, In, Sn, La, and Ce. These positive electrode active materials may be used singly, or in combination of two or more kinds thereof.

The positive electrode active material preferably contains a lithium-containing composite oxide represented by the following Formula (C1) (hereinafter, may be referred to as "NCM"). The lithium-containing composite oxide (C1) is advantageous in that it has a high energy density per unit volume and excellent thermal stability.

$$LiNi_aCo_bMn_cO_2 \quad (C1)$$

In Formula (C1), each of a, b, and c independently represents a number larger than 0 but smaller than 1, and a sum of a, b, and c is from 0.99 to 1.00.

Specific examples of the NCM include $LiNi_{0.33}Co_{0.33}Mn_{0.33}O_2$, $LiNi_{0.5}Co_{0.3}Mn_{0.2}O_2$, $LiNi_{0.6}Co_{0.2}Mn_{0.2}O_2$, and $LiNi_{0.8}Co_{0.1}Mn_{0.1}O_2$.

The positive electrode active material may also contain a lithium-containing composite oxide represented by the following Formula (C2) (hereinafter, may be referred to as "NCA").

$$Li_tNi_{1-x-y}Co_xAl_yO_2 \quad (C2)$$

In Formula (C2), t represents a number of from 0.95 to 1.15, x represents a number of from 0 to 0.3, y represents a number of from 0.1 to 0.2, and a sum of x and y is less than 0.5.

Specific examples of the NCA include $LiNi_{0.8}Co_{0.15}Al_{0.05}O_2$.

When the positive electrode in the lithium secondary battery precursor according to the present embodiment includes a positive electrode current collector and a positive electrode mixture layer that contains a positive electrode active material and a binder, a content of the positive electrode active material is preferably in the below-described range.

A lower limit of the content of the positive electrode active material in the positive electrode mixture layer is preferably 10% by mass or more, more preferably 30% by mass or more, still more preferably 50% by mass or more, particularly preferably 70% by mass or more, with respect to a total amount of the positive electrode mixture layer.

An upper limit of the content of the positive electrode active material in the positive electrode mixture layer is preferably 99.9% by mass or less, more preferably 99% by mass or less, with respect to a total amount of the positive electrode mixture layer.

Examples of the binder include polyvinyl acetate, polymethyl methacrylate, nitrocellulose, fluorine resins, and rubber particles.

Examples of the fluorine resins include polytetrafluoroethylenes (PTFE), polyvinylidene fluorides (PVDF), tetrafluoroethylene-hexafluoropropylene copolymers (FEP), and vinylidene fluoride-hexafluoropropylene copolymers.

Examples of the rubber particles include styrene-butadiene rubber particles and acrylonitrile rubber particles.

Thereamong, from the standpoint of improving the oxidation resistance of the positive electrode mixture layer, the binder is preferably a fluorine resin. The above-described binders may be used singly, or in combination of two or more kinds thereof if necessary.

From the standpoint of satisfying both the physical properties of the positive electrode mixture layer (e.g., electrolyte solution permeability and peeling strength) and the battery performance, the content of the binder in the positive electrode mixture layer is preferably from 0.1% by mass to 4% by mass with respect to a total amount of the positive electrode mixture layer. When the content of the binder is 0.1% by mass or more, the adhesion of the positive electrode mixture layer to the positive electrode current collector and the bindability between positive electrode active materials are further improved. When the content of the binder is 4% by mass or less, the amount of the positive electrode active material in the positive electrode mixture layer can be further increased, so that the battery capacity is further improved.

The positive electrode mixture layer according to the present embodiment preferably contains a conductive aid.

As for a material of the conductive aid, any known conductive aid can be used. The known conductive aid is preferably a conductive carbon material. Examples of the conductive carbon material include graphites, carbon blacks, conductive carbon fibers, and fullerenes. These conductive carbon materials may be used singly, or in combination of two or more kinds thereof. Examples of the conductive carbon fibers include carbon nanotubes, carbon nanofibers, or carbon fibers. Examples of the graphites include artificial graphite and natural graphite. Examples of the natural graphite include flake graphite, bulk graphite, and earthy graphite.

The conductive aid may be a commercially available product. Examples of a commercially available carbon black include: TOKA BLACK #4300, #4400, #4500, #5500 and the like (furnace blacks manufactured by Tokai Carbon Co., Ltd.); PRINTEX L and the like (furnace blacks manufactured by Degussa-Hüls AG); RAVEN 7000, 5750, 5250, 5000 ULTRA III, 5000 ULTRA and the like, CONDUCTEX SC ULTRA, CONDUCTEX 975ULTRA and the like, PURE BLACK 100, 115, 205 and the like (furnace blacks manufactured by Columbian Chemicals Company, Inc.); #2350, #2400B, #2600B, #30050B, #3030B, #3230B, #3350B, #3400B, #5400B and the like (furnace blacks manufactured by Mitsubishi Chemical Corporation); MONARCH 1400, 1300, 900, VULCAN XC-72R, BLACK PEARLS 2000, LITX-50, LITX-200 and the like (furnace blacks manufactured by Cabot Corporation); ENSACO 250G, ENSACO 260G, ENSACO 350G, and SUPER-P (manufactured by Timcal Ltd.); KETJEN BLACK EC-300J and EC-600JD (manufactured by AkzoNobel N.V.); and DENKA BLACK, DENKA BLACK HS-100, and FX-35 (acetylene blacks manufactured by Denka Co., Ltd.).

The positive electrode mixture layer according to the present embodiment may also contain other components. Examples of the other components include a thickening agent, a surfactant, a dispersant, a wetting agent, and an antifoaming agent.

<Negative Electrode>

The negative electrode contains at least one negative electrode active material. The negative electrode active material is capable of occluding and releasing lithium ions.

The negative electrode according to the present embodiment more preferably includes a negative electrode current collector and a negative electrode mixture layer. The negative electrode mixture layer is arranged on at least a portion of the surface of the negative electrode current collector.

A material of the negative electrode current collector is not particularly limited, and any known material can be used as desired. The material of the negative electrode current collector is, for example, a metal or an alloy. More particularly, examples of the material of the negative electrode current collector include aluminum, nickel, stainless steel (SUS), nickel-plated steel, and copper. Thereamong, from the standpoint of workability, the material of the negative electrode current collector is preferably copper. The negative electrode current collector is preferably a copper foil.

The negative electrode mixture layer according to the present embodiment contains a negative electrode active material and a binder.

The negative electrode active material is not particularly limited as long as it is a substance capable of occluding and releasing lithium ions. The negative electrode active material is preferably, for example, at least one selected from the group consisting of metal lithium, lithium-containing alloys, metals and alloys that can be alloyed with lithium, oxides capable of doping and dedoping lithium ions, transition metal nitrides capable of doping and dedoping lithium ions, and carbon materials capable of doping and dedoping lithium ions. Thereamong, the negative electrode active material is preferably a carbon material capable of doping and dedoping lithium ions (hereinafter, simply referred to as "carbon material").

Examples of the carbon material include carbon black, activated charcoal, graphite materials, and amorphous carbon materials. These carbon materials may be used singly, or in combination of two or more kinds thereof as a mixture. The form of the carbon material is not particularly limited and may be, for example, any of a fibrous form, a spherical form, and a flake form. The particle size of the carbon material is also not particularly limited, and it is preferably from 5 μm to 50 μm, more preferably from 20 μm to 30 μm.

Examples of the amorphous carbon materials include hard carbon, cokes, mesocarbon microbeads (MCMB) calcined at 1,500° C. or lower, and mesophase pitch carbon fibers (MCF).

Examples of the graphite materials include natural graphite and artificial graphite. Examples of the artificial graphite include graphitized MCMB and graphitized MCF. The graphite materials may contain boron. The graphite materials may be coated with a metal or amorphous carbon as well. Examples of the metal used for coating the graphite materials include gold, platinum, silver, copper, and tin. The graphite materials may be mixtures of amorphous carbon and graphite.

The negative electrode mixture layer according to the present embodiment preferably contains a conductive aid. Examples of the conductive aid include the same ones as those exemplified above as the conductive aid that may be contained in the positive electrode mixture layer.

The negative electrode mixture layer according to the present embodiment may also contain other components in addition to the above-described components. Examples of the other components include a thickening agent, a surfactant, a dispersant, a wetting agent, and an antifoaming agent.

<Separator>

The separator is, for example, a porous resin plate. Examples of a material of the porous resin plate include resins and nonwoven fabrics containing the resins. Examples of the resins include polyethylene (PE), polypropylene (PP), polymethylpentene (PMP), polyester, cellulose, and polyamide.

Particularly, the separator is preferably a porous resin sheet having a monolayer or multilayer structure. The material of the porous resin sheet is mainly composed of one or more kinds of polyolefin resins. The thickness of the separator is preferably from 5 μm to 30 μm. The separator is preferably arranged between the positive electrode and the negative electrode.

[One Example of Lithium Secondary Battery Precursor]

Referring to FIG. 1, one example of a lithium secondary battery precursor 1 according to one embodiment of the disclosure will now be described concretely. FIG. 1 is a cross-sectional view of the lithium secondary battery precursor 1 according to one embodiment of the disclosure.

The lithium secondary battery precursor 1 is of a layered type. As illustrated in FIG. 1, the lithium secondary battery precursor 1 includes a battery element 10, a positive electrode lead 21, a negative electrode lead 22, and an outer package 30. The battery element 10 is enclosed in the outer package 30. The outer package 30 is formed of a laminated film. The positive electrode lead 21 and the negative electrode lead 22 are each attached to the battery element 10. The positive electrode lead 21 and the negative electrode lead 22 are drawn out in the opposite direction to each other from the inside of the outer package 30 to the outside.

In the battery element 10 according to the present embodiment, as illustrated in FIG. 1, a positive electrode 11, a separator 13, and a negative electrode 12 are disposed in layers. In the positive electrode 11, a positive electrode mixture layer 11B is formed on both main surfaces of a positive electrode current collector 11A. In the negative electrode 12, a negative electrode mixture layer 12B is formed on both main surfaces of a negative electrode current collector 12A. The positive electrode mixture layer 11B formed on one of the main surfaces of the positive electrode current collector 11A of the positive electrode 11 and the negative electrode mixture layer 12B formed on one of the main surfaces of the negative electrode current collector 12A of the negative electrode 12 adjacent to the positive electrode 11 face each other via the separator 13.

Inside the outer package 30 of the lithium secondary battery precursor 1, the nonaqueous electrolyte solution according to the present embodiment is injected. The nonaqueous electrolyte solution according to the present embodiment is impregnated into the positive electrode mixture layer 11B, the separator 13, and the negative electrode mixture layer 12B. In the lithium secondary battery precursor 1, a single cell layer 14 is formed by the positive electrode mixture layer 11B, the separator 13, and the negative electrode mixture layer 12B that are adjacent to one another. In the positive electrode 11, the positive electrode mixture layer 11B may be formed on only one of the main surfaces of the positive electrode current collector 11A, and, in the negative electrode 12, the negative electrode mixture layer 12B may be formed on only one of the main surfaces of the negative electrode current collector 12A.

It is noted here that, although the lithium secondary battery precursor 1 of the present embodiment is of a layered type, the disclosure is not limited thereto, and the lithium secondary battery precursor 1 may be of, for example, a wound type. The lithium secondary battery precursor 1 of a wound type is obtained by disposing the positive electrode, the separator, the negative electrode, and the separator on one another in this order, and winding the resultant in a layered form. The wound type encompasses a cylindrical shape and a prismatic shape.

In the present embodiment, as illustrated in FIG. 1, the directions in which the positive electrode lead 21 and the negative electrode lead 22 each protrude from the inside of the outer package 30 to the outside are opposite to each other with respect to the outer package 30; however, the disclosure is not limited to this mode. For example, the directions in which the positive electrode lead and the negative electrode lead each protrude from the inside of the outer package 30 to the outside may be the same with respect to the outer package 30.

One example of the below-described lithium secondary battery according to one embodiment of the disclosure is a lithium secondary battery of a mode in which an SEI film and the like are formed on the surface of each of the positive electrode mixture layer 11B and the negative electrode mixture layer 12B in the lithium secondary battery precursor 1 by charging and discharging of the lithium secondary battery precursor 1.

[Lithium Secondary Battery]

The lithium secondary battery according to one embodiment of the disclosure will now be described.

The lithium secondary battery according to the present embodiment is obtained by charging and discharging a lithium secondary battery precursor.

Particularly, the lithium secondary battery according to the present embodiment includes a casing, a positive electrode, a negative electrode, a separator, and an electrolyte solution. The positive electrode, the negative electrode, the separator, and the electrolyte solution are housed in the casing. The positive electrode is capable of occluding and releasing lithium ions. The negative electrode is also capable of occluding and releasing lithium ions. The electrolyte solution is the nonaqueous electrolyte solution according to the present embodiment. The negative electrode includes an SEI film. The positive electrode includes a CEI film.

The lithium secondary battery according to the present embodiment is different from the lithium secondary battery precursor according to the present embodiment mainly in terms of a first point that the negative electrode includes an SEI film, and a second point that the positive electrode includes a CEI film. In other words, the lithium secondary battery according to the present embodiment is the same as the lithium secondary battery precursor according to the present embodiment, except for the first and the second points. Therefore, with regard to the lithium secondary battery according to the present embodiment, descriptions of constituent members other than the first and the second points are omitted below.

With regard to the first point, when the negative electrode includes a negative electrode current collector and a negative electrode mixture layer, the feature that "the negative electrode includes an SEI film" encompasses a first negative electrode form and a second negative electrode form. The first negative electrode form represents a form in which the SEI film is formed on at least a portion of the surface of the negative electrode mixture layer. The second negative electrode form represents a form in which the SEI film is formed on the surface of a negative electrode active material that is a constituent of the negative electrode mixture layer.

With regard to the second point, when the positive electrode includes a positive electrode current collector and a positive electrode mixture layer, the feature that "the positive electrode includes a CEI film" encompasses a first positive electrode form and a second positive electrode form. The first positive electrode form represents a form in which the CEI film is formed on at least a portion of the surface of the positive electrode mixture layer. The second positive electrode form represents a form in which the CEI film is formed on the surface of a positive electrode active material that is a constituent of the positive electrode mixture layer.

The SEI film contains, for example, at least one selected from the group consisting of a decomposition product of the nitrogen-containing lithium salt compound (I), a decomposition product of the cyclic sulfur-containing ester compound (II), a reaction product of the nitrogen-containing lithium salt compound (I) or the cyclic sulfur-containing ester compound (II) and an electrolyte, and a decomposition product of the reaction product.

The CEI film contains, for example, at least one selected from the group consisting of a decomposition product of the nitrogen-containing lithium salt compound (I), a decomposition product of the cyclic sulfur-containing ester compound (II), a reaction product of the nitrogen-containing lithium salt compound (I) or the cyclic sulfur-containing ester compound (II) and an electrolyte, and a decomposition product of the reaction product.

A component of the SEI film and a component of the CEI film may be the same or different from each other. The thickness of the SEI film and that of the CEI film may also be the same or different from each other.

[Method of Producing Lithium Secondary Battery Precursor]

Next, a method of producing the lithium secondary battery precursor according to one embodiment of the disclosure will be described.

The method of producing the lithium secondary battery precursor according to the present embodiment includes: the first preparation step; the second preparation step; the third preparation step; the housing step; and the injection step. The housing step and the injection step are carried out in this order. The first preparation step, the second preparation step, and the third preparation step are each carried out prior to the housing step.

In the first preparation step, a positive electrode is prepared.

Examples of a method of preparing the positive electrode include a method of applying and then drying a positive electrode mixture slurry onto the surface of a positive electrode current collector. The positive electrode mixture slurry contains a positive electrode active material and a binder.

As a solvent contained in the positive electrode mixture slurry, an organic solvent is preferred. Examples of the organic solvent include N-methyl-2-pyrrolidone (NMP).

A method of applying the positive electrode mixture slurry is not particularly limited, and examples thereof include slot die coating, slide coating, curtain coating, and gravure coating. A method of drying the positive electrode mixture slurry is also not particularly limited, and examples thereof include drying with warm air, hot air, or low-humidity air; vacuum-drying; and drying by irradiation with infrared radiation (e.g., far-infrared radiation). The drying time is not particularly limited, and it is preferably from 1 minute to 30 minutes. The drying temperature is also not particularly limited, and it is preferably from 40° C. to 80° C.

A dry product obtained by applying and drying the positive electrode mixture slurry on the positive electrode current collector is preferably subjected to a press treatment. By this, the porosity of the resulting positive electrode active material layer is reduced. As a method of the press treatment, for example, mold pressing or roll pressing can be employed.

In the second preparation step, a negative electrode is prepared.

Examples of a method of preparing the negative electrode include a method of applying and then drying a negative electrode mixture slurry onto the surface of a negative electrode current collector. The negative electrode mixture slurry contains a negative electrode active material and a binder.

Examples of a solvent contained in the negative electrode mixture slurry include water and a liquid medium compatible with water. When the solvent contained in the negative electrode mixture slurry contains a liquid medium compatible with water, the applicability of the mixture slurry to the negative electrode current collector can be improved. Examples of the liquid medium compatible with water include alcohols, glycols, cellosolves, aminoalcohols, amines, ketones, carboxylic acid amides, phosphoric acid amides, sulfoxides, carboxylic acid esters, phosphoric acid esters, ethers, and nitriles.

Examples of an application method, a drying method, and a press treatment of the negative electrode mixture slurry include the same methods as those exemplified above for the positive electrode mixture slurry.

In the third preparation step, a nonaqueous electrolyte solution is prepared.

A method of preparing the nonaqueous electrolyte solution includes, for example, the step of dissolving an electrolyte in a nonaqueous solvent to obtain a solution, and the step of adding the nitrogen-containing lithium salt compound (I) and the cyclic sulfur-containing ester compound (II) to the thus obtained solution and subsequently mixing the resultant to obtain a nonaqueous electrolyte solution.

In the housing step, the positive electrode, the negative electrode, and a separator are housed in a casing.

In the housing step, for example, a battery element is produced using the positive electrode, the negative electrode, and the separator. Subsequently, the positive electrode current collector of the positive electrode and a positive electrode lead are electrically connected, and the negative electrode current collector of the negative electrode and a negative electrode lead are electrically connected. Thereafter, the resulting battery element is housed and immobilized in the casing.

A method of electrically connecting the positive electrode current collector and the positive electrode lead is not particularly limited, and examples thereof include ultrasonic welding and resistance welding. A method of electrically connecting the negative electrode current collector and the negative electrode lead is also not particularly limited, and examples thereof include ultrasonic welding and resistance welding.

A state where the positive electrode, the negative electrode, and the separator are housed in the casing is hereinafter referred to as "assembly".

In the injection step, the nonaqueous electrolyte solution according to the present embodiment is injected into the assembly. By this, the nonaqueous electrolyte solution is allowed to permeate into the positive electrode mixture layer 11B, the separator 13, and the negative electrode mixture layer 12B. As a result, a lithium secondary battery precursor is obtained.

[Method of Producing Lithium Secondary Battery]

Next, the method of producing a lithium secondary battery according to one embodiment of the disclosure will be described.

The method of producing a lithium secondary battery according to the present embodiment includes the fourth preparation step and the aging step. The fourth preparation step and the aging step are carried out in this order.

In the fourth preparation step, a lithium secondary battery precursor is prepared. A method of preparing the lithium secondary battery precursor is the same as the above-described method of producing a lithium secondary battery precursor.

In the aging step, the lithium secondary battery precursor is subjected to an aging treatment. By this, an SEI film and a CEI film are formed. In other words, a lithium secondary battery is obtained.

The aging treatment includes charging and discharging the lithium secondary battery precursor in an environment of from 25° C. to 70° C. Particularly, the aging treatment includes: a first charging phase; a first retention phase; a second charging phase; a second retention phase; and a charge-discharge phase.

In the first charging phase, the lithium secondary battery precursor is charged in an environment of from 25° C. to 70° C. In the first retention phase, the lithium secondary battery precursor after the first charging phase is maintained in an environment of from 25° C. to 70° C. In the second charging phase, the lithium secondary battery precursor after the first retention phase is charged in an environment of from 25° C. to 70° C. In the second retention phase, the lithium secondary battery precursor after the second charging phase is maintained in an environment of from 25° C. to 70° C. In the charge-discharge phase, the lithium secondary battery precursor after the second retention phase is subjected to a combination of charging and discharging at least once in an environment of from 25° C. to 70° C.

In the lithium secondary battery obtained by the method of producing a lithium secondary battery according to the present embodiment, an effect of inhibiting a decrease in the capacity and an increase in the internal resistance of the lithium secondary battery is more effectively exerted even when the lithium secondary battery is stored in a high-temperature environment over an extended period.

EXAMPLES

Embodiments of the disclosure will now be described in detail referring to Examples. It is noted here, however, that the disclosure is not limited to the below-described Examples by any means.

Example 1-1

A nonaqueous electrolyte solution was obtained in the following manner.

(Preparation of Nonaqueous Electrolyte Solution)

Ethylene carbonate (EC), dimethyl carbonate (DMC), and ethyl methyl carbonate (EMC) were mixed at EC:DMC:

EMC=30:35:35 (volume ratio). By this, a mixed solvent (nonaqueous solvent) was obtained as a nonaqueous solvent.

In the thus obtained mixed solvent, $LiPF_6$ (electrolyte) was dissolved such that the concentration thereof in a nonaqueous electrolyte solution to be eventually obtained would be 1 mol/L, whereby an electrolyte solution was obtained.

The thus obtained electrolyte solution is hereinafter referred to as "basic electrolyte solution".

As additives, lithium diethylsulfamate (I-1), cyclic sulfur-containing ester compound (IIa-1), cyclic sulfur-containing ester compound (IIa-2), lithium bis(oxalato)borate (III-1), and vinylene carbonate (IV-1) were added to the basic electrolyte solution such that the content (% by mass) of each additive with respect to a total amount of a nonaqueous electrolyte solution to be eventually obtained would be as shown in Table 1. By this, a nonaqueous electrolyte solution was obtained.

(I-1)

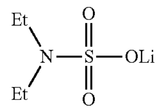

(IIa-1)

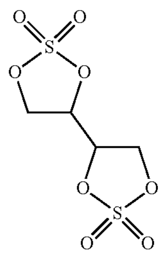

(IIa-2)

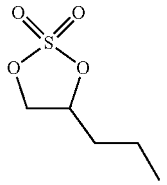

(III-1)

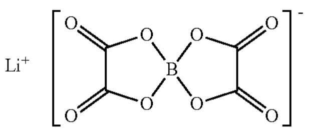

(IV-1)

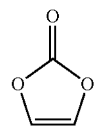

<Production of Lithium Secondary Battery Precursor>

An aluminum laminate-type battery was produced as a lithium secondary battery precursor in the following manner.

(First Preparation Step)

A positive electrode was prepared in the following manner.

A mixture, which was obtained by adding 94% by mass of $Li(Ni_{0.5}Co_{0.2}Mn_{0.3}O_2)$ as a positive electrode active material, 3% by mass of carbon black as a conductive aid, and 3% by mass of polyvinylidene fluoride (PVDF) as a binder, was dispersed in an N-methylpyrrolidone solvent to obtain a positive electrode mixture slurry.

The thus obtained positive electrode mixture slurry was applied and dried onto a 20 μm-thick aluminum foil (positive electrode current collector), and the resultant was subsequently roll-pressed using a press machine to obtain a positive electrode raw sheet. This positive electrode raw sheet includes a region where a positive electrode active material mixture layer (hereinafter, referred to as "positive electrode mixture layer") is formed and a region where the positive electrode mixture layer is not formed (this region is hereinafter referred to as "uncoated part for tab adhesion"). The uncoated part for tab adhesion is an uncoated part that serves as a margin.

The thus obtained positive electrode raw sheet was slit to obtain a positive electrode. This positive electrode had a positive electrode mixture layer and an uncoated part for tab adhesion. The positive electrode mixture layer had a size of 29 mm in width and 40 mm in length. The uncoated part for tab adhesion had a size of 5 mm in width and 11 mm in length.

(Second Preparation Step)

A negative electrode was prepared in the following manner.

A negative electrode mixture slurry was obtained by adding and mixing 96% by mass of graphite as a negative electrode active material, 1% by mass of carbon black as a conductive aid, sodium carboxymethyl cellulose dispersed in pure water as a thickening agent in an amount of 1% by mass in terms of solid content, and a styrene-butadiene rubber (SBR) dispersed in pure water as a binder in an amount of 2% by mass in terms of solid content.

The thus obtained slurry was applied and dried onto a 10 μm-thick copper foil (negative electrode current collector), and the resultant was subsequently roll-pressed using a press machine to obtain a negative electrode raw sheet. This negative electrode raw sheet includes a region where a negative electrode active material mixture layer (hereinafter, referred to as "negative electrode mixture layer") is formed and a region where the negative electrode mixture layer is not formed (this region is hereinafter referred to as "uncoated part for tab adhesion"). The uncoated part for tab adhesion is an uncoated part that serves as a margin.

The thus obtained negative electrode raw sheet was slit to obtain a negative electrode. This negative electrode had a negative electrode mixture layer and an uncoated part for tab adhesion. The negative electrode mixture layer had a size of 30 mm in width and 41 mm in length. The uncoated part for tab adhesion had a size of 5 mm in width and 11 mm in length.

(Third Preparation Step)

The nonaqueous electrolyte solution obtained in the above-described "Preparation of Nonaqueous Electrolyte Solution" was prepared.

(Housing Step)

As a separator, a porous polypropylene film was prepared.

The positive electrode, the negative electrode, and the separator were disposed in layers in an orientation that the coated surface of the negative electrode was in contact with the separator and the coated surface of the positive electrode was in contact with the separator, whereby a layered body was obtained. Subsequently, using an ultrasonic bonding machine, a positive electrode tab made of aluminum (positive electrode lead) was bonded to the uncoated part for tab adhesion of the positive electrode of the thus obtained layered body. Further, using an ultrasonic bonding machine, a negative electrode tab made of nickel (negative electrode lead) was bonded to the uncoated part for tab adhesion of the positive electrode of the thus obtained layered body. The layered body to which the positive electrode tab and the negative electrode tab were thus bonded was sandwiched between a pair of laminated films (casing) obtained by coating both surfaces of an aluminum sheet with resin layers, after which three sides of the resultant were heat-sealed to obtain a laminated body (assembly). In this process, the positive electrode tab and the negative electrode tab were arranged such that they protrude from one of the three sealed sides of the laminated body, which was in contact with the unsealed opening.

(Injection Step)

From the opening of the laminated body, 0.3 mL of the above-obtained nonaqueous electrolyte solution was injected, and the opening of the laminated body was sealed. By this, an aluminum laminate-type battery (lithium secondary battery precursor) was obtained.

Examples 1-2 to 3-2 and Comparative Examples 1-1 to 3-1

Aluminum laminate-type batteries (lithium secondary battery precursors) were obtained in the same manner as in Example 1-1, except that the contents of lithium diethylsulfamate (I-1), cyclic sulfur-containing ester compound (IIa-1), cyclic sulfur-containing ester compound (IIa-2), lithium bis(oxalato)borate (III-1), and vinylene carbonate (IV-1) were changed as shown in Table 1.

[Evaluation Tests]

Each of the thus obtained aluminum laminate-type batteries was subjected to the below-described aging treatment to obtain a first battery. The below-described initial charge-discharge treatment was performed on the thus obtained first battery to obtain a second battery. The thus obtained second battery was subjected to the below-described treatment for evaluation of direct-current resistance to obtain a third battery, which was subsequently subjected to a high-temperature storage treatment to obtain a fourth battery. The thus obtained fourth battery was subjected to the below-described late charge-discharge treatment to obtain a fifth battery. Using the thus obtained first to fifth batteries, the capacity after high-temperature storage and the resistance after high-temperature storage were measured in accordance with the respective measurement methods described below. The results thereof are shown in Tables 1 to 3.

<Aging Treatment>

Each aluminum laminate-type battery was subjected to the following aging treatment to obtain a first battery.

The battery precursor was charged to a final voltage range of from 1.5 V to 3.5 V in a temperature range of from 25 to 70° C. and then rested for a period ranging from 5 to 50 hours. Subsequently, the battery precursor was charged to a final voltage range of from 3.5 V to 4.2 V in a temperature range of from 25 to 70° C. and then maintained for a period ranging from 5 to 50 hours. Thereafter, the battery precursor was charged to 4.2 V in a temperature range of from 25 to 70° C. and then discharged to 2.5 V, whereby a first battery was obtained.

<Initial Charge-Discharge Treatment>

The first battery was subjected to the following initial charge-discharge treatment to obtain a second battery.

The first battery was maintained in a temperature environment of 25° C. for 12 hours. Subsequently, the first battery was constant-current constant-voltage charged at a charge rate of 0.2 C (0.2 C-CCCV) up to 4.2 V (SOC (State of Charge) 100%), rested for 30 minutes, and then constant-current discharged at a discharge rate of 0.2 C (0.2 C-CC) to 2.5 V. These operations were performed for a total of three cycles to stabilize the first battery. Thereafter, the first battery was constant-current constant-voltage charged at a charge rate of 0.2 C (0.5 C-CCCV) up to 4.2 V, rested for 30 minutes, and then constant-current discharged at a discharge rate of 1 C (1 C-CC) to 2.5 V, whereby a second battery was obtained.

<Treatment for Evaluation of Direct-Current Resistance>

The second battery was subjected to the following treatment for evaluation of direct-current resistance to obtain a third battery.

The treatment for evaluation of direct-current resistance was performed in a temperature environment of 25° C. The second battery was subjected to CC discharging to 2.5 V at a discharge rate of 0.5 C and then CCCV charging up to 3.7 V at a charge rate of 0.5 C. The term "CCCV charging" used herein means to perform charging at a constant current and a constant voltage.

Subsequently, the second battery was subjected to CC10s discharging at a discharge rate of 1 C and then CC10s charging at a charge rate of 1 C. The term "CC10s discharging" used herein means to perform discharging at a constant current for 10 seconds. The term "CC10s charging" used herein means to perform charging at a constant current for 10 seconds.

Next, the second battery was subjected to CC10s discharging at a discharge rate of 2 C and subsequent CC20s charging at a charge rate of 1 C.

Then, the second battery was subjected to CC10s discharging at a discharge rate of 3 C and subsequent CC30s charging at a charge rate of 1 C.

Further, the second battery was subjected to CC10s discharging at a discharge rate of 4 C and subsequent CC40s charging at a charge rate of 1 C.

Thereafter, the second battery was subjected to CC10s discharging at a discharge rate of 5 C and subsequent CC50s charging at a charge rate of 1 C, whereby a third battery was obtained.

<High-Temperature Storage Treatment>

The third battery was subjected to the following high-temperature storage treatment to obtain a fourth battery.

The third battery was constant-current charged up to 4.2 V at a charge rate of 0.2 C in a temperature environment of 25° C. Subsequently, the third battery in a charged state was left to stand for 28 days in a 60° C. atmosphere. By this, a fourth battery was obtained.

<Late Charge-Discharge Treatment>

The fourth battery was subjected to the following late charge-discharge treatment to obtain a fifth battery.

The fourth battery was allowed to dissipate the heat in a temperature environment of 25° C. and subjected to first discharging and then first charging, followed by second discharging. The first discharging refers to that the fourth battery was constant-current discharged at a discharge rate of 1 C (1 C-CC) to 2.5 V. The first charging refers to that the fourth battery was constant-current constant-voltage charged at a charge rate of 0.2 C (0.2 C-CCCV) up to 4.2 V. The second discharging refers to that the fourth battery was constant-current discharged at a discharge rate of 1 C (1 C-CC) to 2.5 V. A fifth battery was obtained as a result.

<Method of Measuring Capacity after High-Temperature Storage>

As indicated by the below-described equation (X1), a relative value of the capacity of each fourth battery of Comparative Examples 1-2 and 1-3 and Examples 1-1 to 1-5 after high-temperature storage with respect to the capacity of the fourth battery of Comparative Example 1-1 after high-temperature storage was defined as "capacity after high-temperature storage [%]" (see Table 1).

As indicated by the below-described equation (X1), a relative value of the capacity of each fourth battery of Examples 2-1 and 2-2 after high-temperature storage with respect to the capacity of the fourth battery of Comparative Example 2-1 after high-temperature storage was defined as "capacity after high-temperature storage [%]" (see Table 2).

As indicated by the below-described equation (X1), a relative value of the capacity of each fourth battery of Examples 3-1 and 3-2 after high-temperature storage with respect to the capacity of the fourth battery of Comparative Example 3-1 after high-temperature storage was defined as "capacity after high-temperature storage [%]" (see Table 3).

The capacity after high-temperature storage represents the capacity that was obtained when the second discharging was performed in the above-described charge-discharge treatment.

Capacity after high-temperature storage [relative value; %]=(Capacity of fourth battery after high-temperature storage [mAh/g]/Capacity of fourth battery of Comparative Example 1 after high-temperature storage [mAh/g])×100 (X1)

<Method of Measuring Resistance after High-Temperature Storage>

As indicated by the below-described equation (X2), a relative value of the direct-current resistance (DCIR: direct-current internal resistance) of each fifth battery of Comparative Examples 1-2 and 1-3 and Examples 1-1 to 1-5 with respect to the direct-current resistance (DCIR) of the fifth battery of Comparative Example 1-1 was defined as "resistance after high-temperature storage [%]" (see Table 1).

As indicated by the below-described equation (X2), a relative value of the direct-current resistance (DCIR) of each fifth battery of Examples 2-1 and 2-2 with respect to the direct-current resistance (DCIR) of the fifth battery of Comparative Example 2-1 was defined as "resistance after high-temperature storage [%]" (see Table 2).

As indicated by the below-described equation (X2), a relative value of the direct-current resistance (DCIR) of each fifth battery of Examples 3-1 and 3-2 with respect to the direct-current resistance (DCIR) of the fifth battery of Comparative Example 3-1 was defined as "resistance after high-temperature storage [%]" (see Table 3).

Resistance after high-temperature storage [relative value; %]=(Direct-current resistance of fifth battery [Ω]/Direct-current resistance of fifth battery of Comparative Example 1 [Ω])×100 (X2)

The direct-current resistance was measured by the following method. The fifth battery was subjected to the same treatment for evaluation of direct-current resistance as the one described above.

The direct-current resistance (Ω) of the fifth battery was determined based on the amount of decrease in voltage due to "CC10s discharging" at each discharge rate of 1 C to 5C (=voltage before the initiation of discharging-voltage at the 10th second after the initiation of discharging) and each current value (i.e. the current value corresponding to each discharge rate of 1 C to 5 C).

TABLE 1

| | Aqueous electrolyte solution for lithium secondary battery Content of additives | | | | | Lithium secondary battery | |
|---|---|---|---|---|---|---|---|
| | (I) | (II) | | (III) | (IV) | Capacity | Resistance |
| | (I-1) (% by mass) | (IIa-1) (% by mass) | (IIa-2) (% by mass) | (IIII-1) (% by mass) | (IV-1) (% by mass) | after high-temperature storage [%] | after high-temperature storage [%] |
| Comparative Example 1-1 | 0.5 | — | — | — | — | 100 | 100 |
| Comparative Example 1-2 | — | 0.5 | — | — | — | 100 | 92 |
| Comparative Example 1-3 | — | — | 0.5 | — | — | 99 | 101 |
| Example 1-1 | 0.5 | 0.5 | — | — | — | 102 | 87 |
| Example 1-2 | 0.5 | 0.5 | — | 0.5 | — | 105 | 84 |
| Example 1-3 | 0.5 | — | 0.5 | 0.5 | — | 104 | 84 |
| Example 1-4 | 0.5 | 0.5 | — | 0.5 | 0.5 | 105 | 81 |
| Example 1-5 | 0.5 | — | 0.5 | 0.5 | 0.5 | 105 | 81 |

TABLE 2

| | Aqueous electrolyte solution for lithium secondary battery Content of additives | | | | | Lithium secondary battery | |
|---|---|---|---|---|---|---|---|
| | (I) | (II) | | (III) | (IV) | Capacity | Resistance |
| | (I-1) (% by mass) | (IIa-1) (% by mass) | (IIa-2) (% by mass) | (IIII-1) (% by mass) | (IV-1) (% by mass) | after high-temperature storage [%] | after high-temperature storage [%] |
| Comparative Example 2-1 | 0.01 | — | — | — | — | 100 | 100 |

TABLE 2-continued

| | Aqueous electrolyte solution for lithium secondary battery Content of additives | | | | | Lithium secondary battery | |
|---|---|---|---|---|---|---|---|
| | (I) | (II) | | (III) | (IV) | Capacity | Resistance |
| | (I-1) (% by mass) | (IIa-1) (% by mass) | (IIa-2) (% by mass) | (IIII-1) (% by mass) | (IV-1) (% by mass) | after high-temperature storage [%] | after high-temperature storage [%] |
| Example 2-1 | 0.01 | 0.01 | — | — | — | 101 | 97 |
| Example 2-2 | 0.01 | — | 0.01 | — | — | 101 | 98 |

TABLE 3

| | Aqueous electrolyte solution for lithium secondary battery Content of additives | | | | | Lithium secondary battery | |
|---|---|---|---|---|---|---|---|
| | (I) | (II) | | (III) | (IV) | Capacity | Resistance |
| | (I-1) (% by mass) | (IIa-1) (% by mass) | (IIa-2) (% by mass) | (IIII-1) (% by mass) | (IV-1) (% by mass) | after high-temperature storage [%] | after high-temperature storage [%] |
| Comparative Example 3-1 | 0.10 | — | — | — | — | 100 | 100 |
| Example 3-1 | 0.10 | 0.10 | — | — | — | 102 | 92 |
| Example 3-2 | 0.10 | — | 0.10 | — | — | 102 | 93 |

In Tables 1 to 3, "Content of additives" indicates the content [% by mass] of each additive with respect to a total amount of the respective aqueous electrolyte solution for a lithium secondary battery. In Tables 1 to 3, "-" means that the corresponding component was not incorporated.

The nonaqueous electrolyte solutions of Comparative Examples 1-2 and 1-3 contained a cyclic sulfur-containing ester compound (II) or a cyclic dicarbonyl compound (III) singly, and the resistance after high-temperature storage was from 92% to 101% and the capacity after high-temperature storage was from 99% to 100% with respect to those values of the lithium secondary battery of Comparative Example 1-1 which contained a nitrogen-containing lithium salt compound (I) singly. On the other hand, the nonaqueous electrolyte solutions of Examples 1-1 to 1-5 contained both a nitrogen-containing lithium salt compound (I) and a cyclic sulfur-containing ester compound (II); therefore, the lithium secondary batteries of Examples 1-1 to 1-5 had a resistance after high-temperature storage of from 81% to 87% and a capacity after high-temperature storage of from 102% to 105% with respect to those values of the lithium secondary battery of Comparative Example 1-1 which did not contain a cyclic sulfur-containing ester compound (II). In other words, it was found that, in the lithium secondary batteries of Examples 1-1 to 1-5, a decrease in the capacity and an increase in the internal resistance were inhibited even when the lithium secondary batteries were stored in a high-temperature environment over an extended period.

As compared to the nonaqueous electrolyte solution of Comparative Example 2-1 which contained a nitrogen-containing lithium salt compound (I) singly, the nonaqueous electrolyte solutions of Examples 2-1 and 2-2, in which a cyclic sulfur-containing ester compound (II) was used in combination with the nitrogen-containing lithium salt compound (I), yielded a resistance after high-temperature storage of from 97% to 98% and a capacity after high-temperature storage of 101%. In other words, it was found that, in the lithium secondary batteries of Examples 2-1 and 2-2, a decrease in the capacity and an increase in the internal resistance were inhibited even when the lithium secondary batteries were stored in a high-temperature environment over an extended period.

As compared to the nonaqueous electrolyte solution of Comparative Example 3-1 which contained a nitrogen-containing lithium salt compound (I) singly, the nonaqueous electrolyte solutions of Examples 3-1 and 3-2, in which a cyclic sulfur-containing ester compound (II) was used in combination with the nitrogen-containing lithium salt compound (I), yielded a resistance after high-temperature storage of from 92% to 93% and a capacity after high-temperature storage of 102%. In other words, it was found that, in the lithium secondary batteries of Examples 3-1 and 3-2, a decrease in the capacity and an increase in the internal resistance were inhibited even when the lithium secondary batteries were stored in a high-temperature environment over an extended period.

The disclosure of Japanese Patent Application No. 2021-015328 filed on Feb. 2, 2021, is hereby incorporated by reference in its entirety.

All the documents, patent applications, and technical standards that are described in the present specification are hereby incorporated by reference to the same extent as if each individual document, patent application, or technical standard is specifically and individually described to be incorporated by reference.

The invention claimed is:

1. A nonaqueous electrolyte solution for a lithium secondary battery, the solution comprising:

a compound (I) represented by the following Formula (I); and a compound (II) represented by the following Formula (II):

(I)

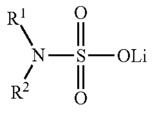

wherein, in Formula (I):

each of $R^1$ and $R^2$ independently represents a substituent that is:

—H,

—F, a group represented by the Formula: $—O_p—(SiR^{11}_2O)_t—SiR^{12}_3$, wherein each of $R^{11}$ and $R^{12}$ independently represents an alkyl group in which at least one hydrogen atom is optionally substituted with a fluorine atom, an alkenyl group in which at least one hydrogen atom is optionally substituted with a fluorine atom, an alkynyl group in which at least one hydrogen atom is optionally substituted with a fluorine atom, or an aryl group in which at least one hydrogen atom is optionally substituted with a fluorine atom; t represents an integer that is 0 or larger; and p represents 0 or 1, an alkyl group having from 1 to 7 carbon atoms, an alkenyl group having from 2 to 7 carbon atoms, an alkynyl group having from 2 to 7 carbon atoms, an aryl group having from 6 to 15 carbon atoms, a group represented by $—SO_2X^1$, wherein $X^1$ represents —H, —F, or an alkyl group in which at least one hydrogen atom is optionally substituted with a fluorine atom, a group represented by $—SO_3X^2$, wherein $X^2$ represents —H, —F, or an alkyl group in which at least one hydrogen atom is optionally substituted with a fluorine atom, or a hydrocarbon group having from 2 to 7 carbon atoms, in which $R^1$ and $R^2$ are bound to each other to form a cyclic structure that optionally contains a multiple bond, and the substituent has a structure which optionally contains at least one di- to hexa-valent heteroatom, and in which at least one hydrogen atom is optionally substituted with a fluorine atom or a functional group having from 0 to 7 carbon atoms;

(II)

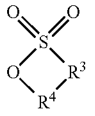

wherein, in Formula (II):

$R^3$ represents an oxygen atom, an alkylene group having from 2 to 6 carbon atoms, or an alkenylene group having from 2 to 6 carbon atoms, $R^4$ represents an alkylene group having from 2 to 6 carbon atoms, an alkenylene group having from 2 to 6 carbon atoms, a group represented by the following Formula (ii-1), or a group represented by the following Formula (ii-2), and

* represents a binding position, (ii-1)

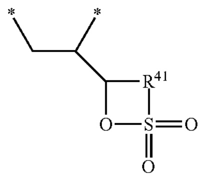

(ii-2)

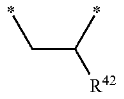

wherein, in Formula (ii-1), $R^{41}$ represents an oxygen atom, an alkylene group having from 1 to 6 carbon atoms, an alkenylene group having from 2 to 6 carbon atoms, or an oxymethylene group, and wherein, in Formula (ii-2), $R^{42}$ represents an alkyl group having from 1 to 6 carbon atoms, or an alkenyl group having from 2 to 6 carbon atoms.

2. The nonaqueous electrolyte solution for a lithium secondary battery according to claim 1, wherein $R^3$ is an oxygen atom.

3. The nonaqueous electrolyte solution for a lithium secondary battery according to claim 1, wherein a content of the compound (I) is from 0.01% by mass to 5% by mass with respect to a total amount of the nonaqueous electrolyte solution for a lithium secondary battery.

4. The nonaqueous electrolyte solution for a lithium secondary battery according to claim 1, wherein a content of the compound (II) is from 0.01% by mass to 5% by mass with respect to a total amount of the nonaqueous electrolyte solution for a lithium secondary battery.

5. The nonaqueous electrolyte solution for a lithium secondary battery according to claim 1, comprising a compound (III) represented by the following Formula (III):

(III)

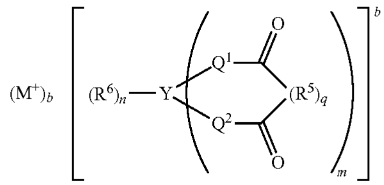

wherein, in Formula (III):

M represents an alkali metal,

Y represents a transition element, or an element of Group 13, 14, or 15 of the periodic table, b represents an integer from 1 to 3, m represents an integer from 1 to 4, n represents an integer from 0 to 8, q represents 0 or 1, $R^5$ represents an alkylene group having from 1 to 10 carbon atoms, a halogenated alkylene group having from 1 to 10 carbon atoms, an arylene group having from 6 to 20 carbon atoms, or a halogenated arylene group having from 6 to 20 carbon atoms, the halogenated alkylene group, the arylene group and the halogenated arylene group each optionally containing a substituent or a heteroatom in structure thereof and, when q is 1 and m is from 2 to 4, m instances of $R^5$ are optionally bound to each other, $R^6$ represents a halogen atom, an alkyl group having from 1 to 10 carbon atoms, a halogenated alkyl group having from 1 to 10 carbon atoms, an aryl group having from 6 to 20 carbon atoms, or a halogenated aryl group having from 6 to 20 carbon atoms, the halogenated alkyl group, the aryl group and the halogenated aryl group each optionally containing a substituent or a heteroatom in a structure thereof and, when n is from 2 to 8, n instances of $R^6$ are optionally bound to each other to form a ring, and each of $Q^1$ and $Q^2$ independently represents an oxygen atom or a carbon atom.

6. The nonaqueous electrolyte solution for a lithium secondary battery according to claim 5, wherein a content of the compound (III) is from 0.01% by mass to 10% by mass with respect to a total amount of the nonaqueous electrolyte solution for a lithium secondary battery.

7. The nonaqueous electrolyte solution for a lithium secondary battery according to claim 1, comprising a compound (IV) represented by the following Formula (IV):

(IV)

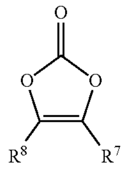

wherein, in Formula (IV), each of $R^7$ and $R^8$ independently represents a hydrogen atom, a methyl group, an ethyl group, or a propyl group.

8. The nonaqueous electrolyte solution for a lithium secondary battery according to claim 7, wherein a content of the compound (IV) is from 0.01% by mass to 10% by mass with respect to a total amount of the nonaqueous electrolyte solution for a lithium secondary battery.

9. A lithium secondary battery precursor, comprising:

a positive electrode;

a negative electrode comprising a negative electrode active material capable of occluding and releasing lithium ions; and the nonaqueous electrolyte solution for a lithium secondary battery according to claim 1.

10. A lithium secondary battery, obtained by charging and discharging the lithium secondary battery precursor according to claim 9.

11. A method of producing a lithium secondary battery, the method comprising:

preparing the lithium secondary battery precursor according to claim 9; and charging and discharging the lithium secondary battery precursor.

* * * * *